United States Patent [19]
Miura et al.

[11] Patent Number: 5,917,031
[45] Date of Patent: Jun. 29, 1999

[54] METHOD OF SYNTHESIZING POLYDEOXYRIBONUCLEOTIDES

[75] Inventors: Takanori Miura, Nara; Norio Ogata, Osaka, both of Japan

[73] Assignee: Taiko Pharmaceutical Co., Ltd., Osaka, Japan

[21] Appl. No.: 08/839,608

[22] Filed: Apr. 15, 1997

[30] Foreign Application Priority Data

Apr. 19, 1996 [JP] Japan .................................. 8-122673
Jun. 18, 1996 [JP] Japan .................................. 8-156647

[51] Int. Cl.$^6$ .......................... C07H 21/00; C07H 21/02; C07H 21/04; C12P 19/34
[52] U.S. Cl. ........................... 536/25.3; 435/6; 435/91.1; 435/91.2; 435/91.5; 536/23.1; 536/24.3; 536/24.1; 536/24.2
[58] Field of Search ............................ 435/5, 6, 18, 91.1, 435/91.2, 91.5; 530/350; 536/23.1, 24.3, 24.31, 24.33, 25.3, 24.1, 24.2

[56] References Cited

U.S. PATENT DOCUMENTS 5,210,036  5/1993  Comb et al. ............................. 435/194
5,352,778  10/1994 Comb et al. ............................. 536/23.2
5,618,711  4/1997  Gelfand et al. ......................... 435/194

FOREIGN PATENT DOCUMENTS 0669401  8/1995  European Pat. Off. .
WO96/07669  3/1996  WIPO .

OTHER PUBLICATIONS

Henner et al, "De novo synthesis of a polymer of deoxyadenylate and deoxythymidylate by calf thymus DNA polymerase alpha", Proc. Natl. Acad. Sci. 72(10):3944–3946, Oct. 1975.

Nazarenko et al, "Study of nature of template free synthesis of d(A–T) copolymer catalyzed by preparations of Escherichi coli DNA polymerase I", Molecular Biology 13(1):163–171, Aug. 1979.

Hanaki et al. "Primer/template independent synthesis of poly d(A–T) by Taq polymerase", Biochem. Biophys. Res. Comm. 238:113–118, 1997.

Clark J.M.: "Novel non–templated nucleotide addition reactions catalyzed by procaryotic DNA polymerases" Nucleic Acids Research, vol. 16, No. 20, 1988, pp. 9677–9686 (XP–002053355).

Database: EMBL Sequences EMBL, Heidelberg, FRG Accession No. L13122, Weber J.L. et al.: "Evidence for human meiotic crossover interference obtained through construction of a short tandem repeat polymorphism linkage map of chromosome 19." (XP002053356), (1993).

(List continued on next page.)

Primary Examiner—Jeffrey Fredman
Attorney, Agent, or Firm—Jordan and Hamburg LLP

[57] ABSTRACT

The invention relates to a method of synthesizing polydeoxyribonucleotides which comprises causing a thermostable deoxyribunucleotide polymerase to act on deoxyribonucleotides without using any template and any primers, to the thus-obtained polydeoxyribonucleotides, to a method of screening cDNA libraries using the same as probes, to a method comprising joining the DNA resulting from the above method of synthesis to the 3'—OH terminus of a double-stranded DNA containing a gene derived from cells of a living organism, followed by transfection of such cells with the product of joining and culture of the cells, to thereby cause insertion of the product into chromosomal DNA and production of the protein encoded by the gene, to a method of synthesizing chromosomal DNA and to a method of synthesizing chromosomes. According to the invention, it is possible to create DNA not occurring in the nature and create novel proteins using the thus created genes, hence means for providing novel physiologically or pharmacologically active substances can be provided.

20 Claims, 10 Drawing Sheets

OTHER PUBLICATIONS

Enzymatic Synthesis of Deoxyribonucleic Acid, VII. Synthesis of a Polymer or Deoxyadenylate and Deoxythymidylate, H.K. Schachman, Julius Adler, Charles M. Radding, I.R. Lehman, and Arthur Kornberg, The Journal of Biological Chemistry, vol. 235, No. 11, Nov. 1960.

Enzymatic Synthesis of Deoxyribonucleic Acid XII. A Polymer of Deoxyguanylate and Deoxyoytidylate, Charles M. Radding, John Josse and Arthur Kornberg, The Journal of Biological Chemistry, vol. 237, No. 9, Sep. 1962.

Enzymatic Synthesis of Deoxyribonucleic Acid XV. Purification and Properties of a Polymerase from Bacillus Subtilis, Tuneko Okazaki and Arthur Kornberg, The Journal of Biological Chemistry, vol. 239, No. 1, Jan. 1964.

Effect of Incubation Conditions on the Nucleotide Sequence of DNA Products of Unprimed DNA Polymerase Reactions, John F. Burd and Robert D. Wells, J. Mol. Biol. (1970) 53, 435.

```
                        SEQUENCE LISTING ( 1 ) GENERAL INFORMATION:

( iii ) NUMBER OF SEQUENCES:  3

( 2 ) INFORMATION FOR SEQ ID NO: 1:

( i ) SEQUENCE CHARACTERISTICS:
           ( A ) LENGTH:  58 nucleic acids
           ( B ) TYPE: nucleic acid
           ( C ) STRANDEDNESS: double strand
           ( D ) TOPOLOGY: linear ( ii ) MOLECULE TYPE: other nucleic acid ( iv ) ANTI-SENSE: yes ( xi ) SEQUENCE DESCRIPTION: SEQ ID NO:1:

TATCTAGATA TCTAGATATATC TAGATATCTA GATATCTAGA TATCTAGATA TCTAGA            58

( 2 ) INFORMATION FOR SEQ ID NO: 2:

( i ) SEQUENCE CHARACTERISTICS:
           ( A ) LENGTH:  34 nucleic acids
           ( B ) TYPE: nucleic acid
           ( C ) STRANDEDNESS: double strand
           ( D ) TOPOLOGY: linear ( ii ) MOLECULE TYPE: other nucleic acid ( iv ) ANTI-SENSE: yes ( xi ) SEQUENCE DESCRIPTION: SEQ ID NO:2:

CTAGATATCT ATCTAGATAT CTATCTAGAT ATCT                                     34

( 2 ) INFORMATION FOR SEQ ID NO: 3:

( i ) SEQUENCE CHARACTERISTICS:
           ( A ) LENGTH:  34 nucleic acids
           ( B ) TYPE: nucleic acid
           ( C ) STRANDEDNESS: double strand
           ( D ) TOPOLOGY: linear ( ii ) MOLECULE TYPE: other nucleic acid ( iv ) ANTI-SENSE: yes ( xi ) SEQUENCE DESCRIPTION: SEQ ID NO:3:

TAGATATCTA GATCTAGATA TCTATCTAGA TATC                                     34
```

METHOD OF SYNTHESIZING POLYDEOXYRIBONUCLEOTIDES

BACKGROUND OF THE INVENTION

1. Technical Field

The present invention relates to a method of non-template-dependent and non-primer-dependent (hereinafter also referred to as "non-template and primer-dependent") synthesis of polydeoxyribonucleotides (DNA). The present invention further relates to a method of synthesizing chromosomal DNA and a method of producing chromosomes and, more particularly, it relates to a method of synthesizing chromosomal DNA and a method of producing chromosomes as established based on the findings that a certain deoxyribonucleotide polymerase (hereinafter briefly referred to as "DNA polymerase") can synthesize DNA not in the manner of "replication", i.e., to copy the genetic information of a template, but in the manner of "creation"; in other words, new pieces of genetic information are made. Some DNA synthesized in that manner serve as centromere, telomere and replication origin which are essential to chromosomal DNA.

2. Prior Art

So far, there have been two principal methods for the synthesis of DNA. One method uses DNA synthetase and the other is a chemical synthesis technique.

The method of synthesizing DNA using DNA synthetase includes so-called template-dependent methods of synthesizing DNA, such as the method of synthesizing DNA from template DNA using DNA polymerase and the method of synthesizing DNA from template RNAs using reverse transcriptase. However, these methods invariably require primers each comprising a short single-stranded DNA or RNA and a single-stranded template DNA for the synthesis of DNA. The so-called polymerase chain reaction (PCR) method, which is a method of amplifying template DNA in an easy and simple manner as developed recently [Saiki et al., Science, volume 239, pages 487–491 (1988)], still requires template DNA and primers.

The chemical method of DNA synthesis includes a phosphodiester method, a phosphotriester method and the like. However, these are complicated in synthetic process, require a lot of time and can synthesize only short DNA. Furthermore, the DNA synthesized are difficult to purify. While some apparatus are already commercially available for such synthesis, they have a drawback in that expensive and special reagents have to be used. The chemical method of synthesis, which has not yet been tried for the creation of DNA, would be substantially incapable of synthesizing DNA of a length of several thousand base pairs (bp). Even if such DNA could be successfully synthesized by said method, it would be expensive. Thus, it can of course be anticipated as well that the creation of proteins by means of the expression of the created DNA would be impossible.

The same applies to the synthesis of chromosomal DNA. Each chromosome possessed by a living organism is composed of a double-stranded linear DNA (chromosomal DNA) and proteins such as histones. Said double-stranded DNA has, as its essential elements, three regions for chromosomal functioning. Said three regions are (1) a centromere region (involved in appropriate partitioning of the replicated chromosome on the occasion of mitosis or meiosis), (2) a telomere region (involved in chromosome stabilization and replication) and (3) a replication start region (autonomously replicating sequence; ARS) (having the property of replication origin and which is involved in the initiation of DNA replication). Lack of any one of said regions makes said chromosomal DNA unstable and allows the disappearance of said DNA in the process of cell division. The total base sequences of the regions (1) to (3) mentioned above are more than 1,000 base pairs and, therefore, it is very difficult to synthesize them throughout to the end.

Therefore, in the prior art, the following technology of producing artificial chromosomes has been proposed. Thus, the technology proposed comprises excising a necessary portion alone from a DNA of living organism origin by a gene recombination technique and joining said portion to another DNA to produce an independent artificial chromosome. Joining, one by one, of the above-mentioned three regions essential to a chromosomal DNA would indeed make it possible to produce an artificial chromosome but the procedure leading thereto is very complicated and low in productivity.

OBJECTS OF THE INVENTION

The object of the present invention is to provide a method to create DNA, or pieces of genetic information, in a non-template and primer-dependent manner. The present invention further has for its object to facilitate the synthesis of double-stranded linear DNA chains (chromosomal DNA) each having the centromere, telomere and replication origin regions, which are essential components of each chromosome, and produce chromosomes using the chromosomal DNA synthesized.

SUMMARY OF THE INVENTION

The method of synthesizing DNA according to the present invention is characterized in that deoxyribonucleotides are polymerized in the absence of a template and/or primers and in the presence of a protein.

The method of synthesizing chromosomal DNA according to the present invention is characterized in that deoxyribonucleotides are polymerized in a reaction system in which the template and/or primers are not present, in the presence of a protein.

DETAILED DESCRIPTION OF THE INVENTION

Figure 1:
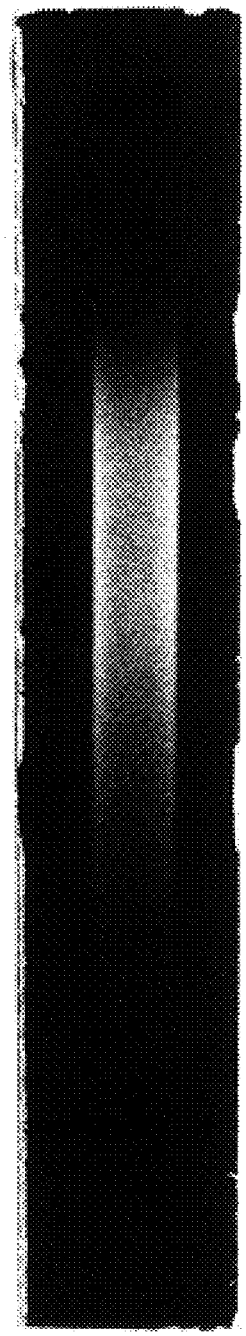
FIG. 1 is a photographic representation of the results of agarose gel electrophoresis (after ethidium bromide staining) of the ntp-DNA synthesized in Example 1.

The present inventors made various discoveries in their studies in DNA synthesis. For example, they kept a reaction mixture composed of *Thermococcus litoralis* DNA polymerase (New England BioLabs), buffer A [10 mM KCl, 10 mM $(NH_4)_2SO_{04}$, 20 mM Tris/HCl (pH 8.8), 6 mM $MgCl_2$, 0.1% Triton X-100 (each in final concentration)] and deoxyribonucleotides [dATP, dCTP, dGTP and dTTP (each in a final concentration of 200 μM)] at 74° C. for 3 hours, and subjected a portion of the reaction mixture to agarose (1%) gel electrophoresis, followed by ethidium bromide staining and observation under an ultraviolet lamp. As a result, DNA bands stained in a wide range of about 1 kbp (1,000 base pairs) to 30 kbp could be identified, as shown in the photograph of FIG. 1.

Then, they prepared a deoxyribonucleotide triphosphate-free reaction mixture, added thereto deoxyribonuclease I or ribonuclease A, and incubated the resulting mixture at 37° C. for 2 hours to completely decompose those DNA or RNAs (each capable of serving as a primer and/or a template) which might be present as contaminants in the reaction mixture and in the enzyme. Then, they added the deoxyribonucleotide triphosphates and carried out the reaction in the same manner as mentioned above. In this case, if the reaction is template- and primer-dependent, then DNA synthesis will never take place. On the other hand, if the reaction is non-template and primer-dependent, DNA synthesis will take place, giving DNA bands identifiable by agarose gel electrophoresis. The results were that bands stained in a wide range of about 1 kbp to 30 kbp could be identified. It was thus confirmed that this reaction is non-template and primer-dependent. In other words, it was revealed that said reaction proceeded independently of DNA or RNAs capable of serving as templates or primers but according to the information possessed by DNA polymerase itself and leading to DNA creation.

Figure 5:
FIG. 5 is a photographic representation of the results of agarose gel electrophoresis, which indicates the synthesis of the ntp-10 kbp DNA as mentioned in Example 6. Line 1—10 kbp ntp-DNA; line 2—ordinary ntp-DNA.

Then, the inventors varied the reaction conditions in the non-template and primer-dependent DNA synthesis using *Thermococcus litoralis* DNA polymerase to thereby examine whether DNA having a size outside the range of about 1 kbp to 30 kbp could be synthesized or not. Thus, deoxyribonuclease I (DNase I) was added to the ordinary reaction mixture, followed by 30 minutes of incubation at 37° C. and the subsequent ordinary three-hour reaction at 74° C. This resulted in the appearance, in the vicinity of 10 kbp, of a DNA band intensely stained with ethidium bromide, as shown in FIG. 5. From this result, it was established that the length of the DNA to be formed can be varied arbitrarily by modifying the reaction conditions.

Figure 6:
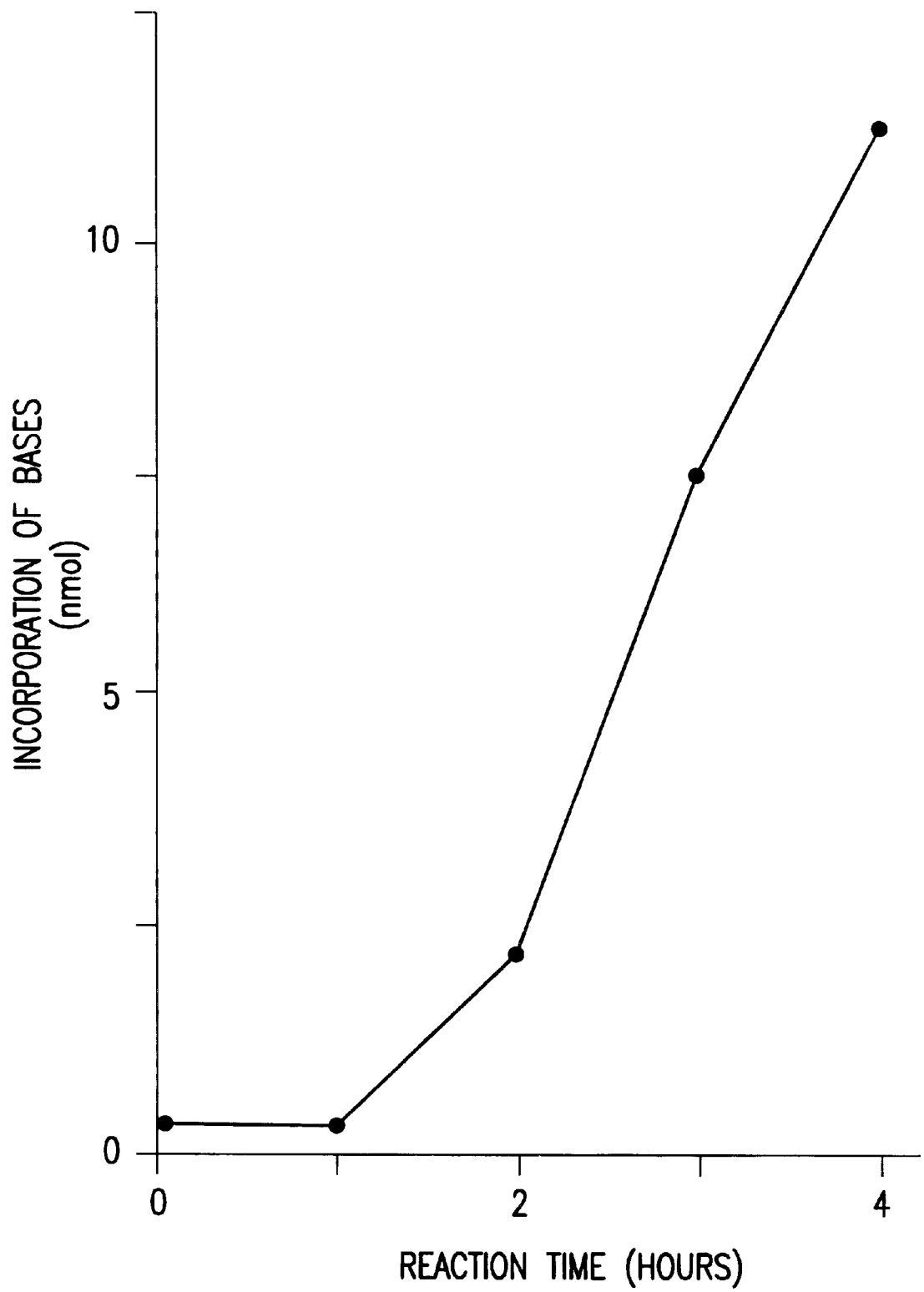
FIG. 6 is a graphic representation of the time course of ntp-DNA synthesis as mentioned in Example 7.

Then, the inventors confirmed the time course of the non-template and primer-dependent synthetic reaction in the presence of *Thermococcus litoralis* DNA polymerase. As shown in FIG. 6, no reaction took place during the first one-hour period (the so-called lag phase) and the reaction started after the lapse of 2 hours. Then, the maximum reaction rate was observed during the period of hour 2 to hour 3. During that period, the rate of reaction was 0.88 bases/second/enzyme molecule. This was one 76th of the rate of ordinary template- and primer-dependent DNA polymerization in the presence of *Thermococcus litoralis* [Kong et al., The Journal of Biological Chemistry, volume 268, pages 1965–1975 (1993)] and one 57th of that attained by *Escherichia coli* DNA polymerase I [Kornberg, DNA Replication, 2nd edition, W. H. Freeman and Company, San Francisco, Calif. (1992)]. Thus, the reaction is considered to be quite different from the ordinary template- and primer-dependent DNA synthesis reaction.

Figure 2:
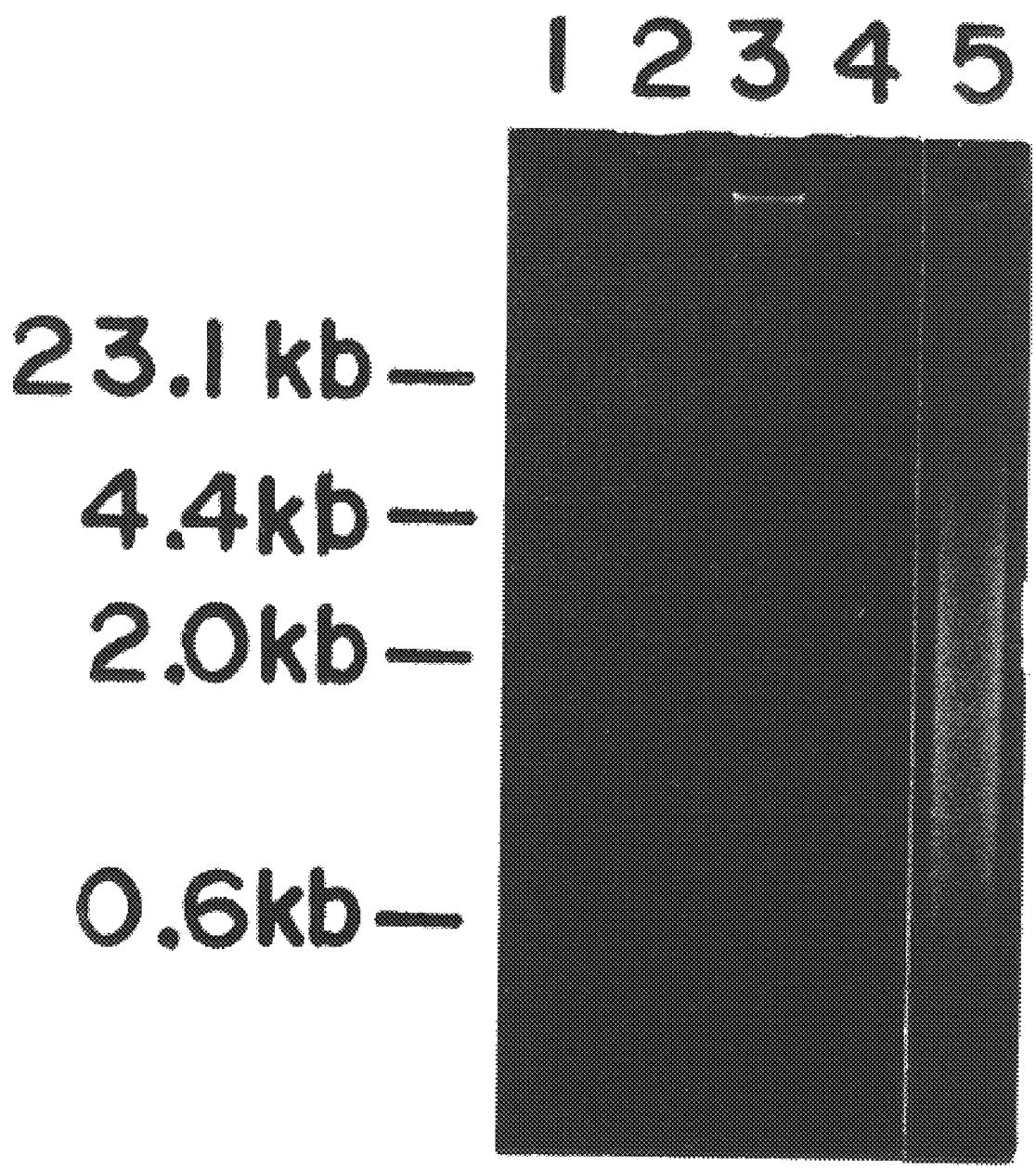
FIG. 2 is a photographic representation of the results of agarose gel electrophoresis illustrating the influence of deoxyribonucleotides in the ntp-DNA synthesis in Example 3. Line 1 corresponds to the ntp-DNA synthesis using dCTP, dGTP and dTTP; line 2—dATP, dGTP and dTTP; line 3—dATP, dCTP and dTTP; line 4—dATP, dCTP and dGTP; and line 5—dATP, dCTP, dGTP and dTTP.
Figure 3:
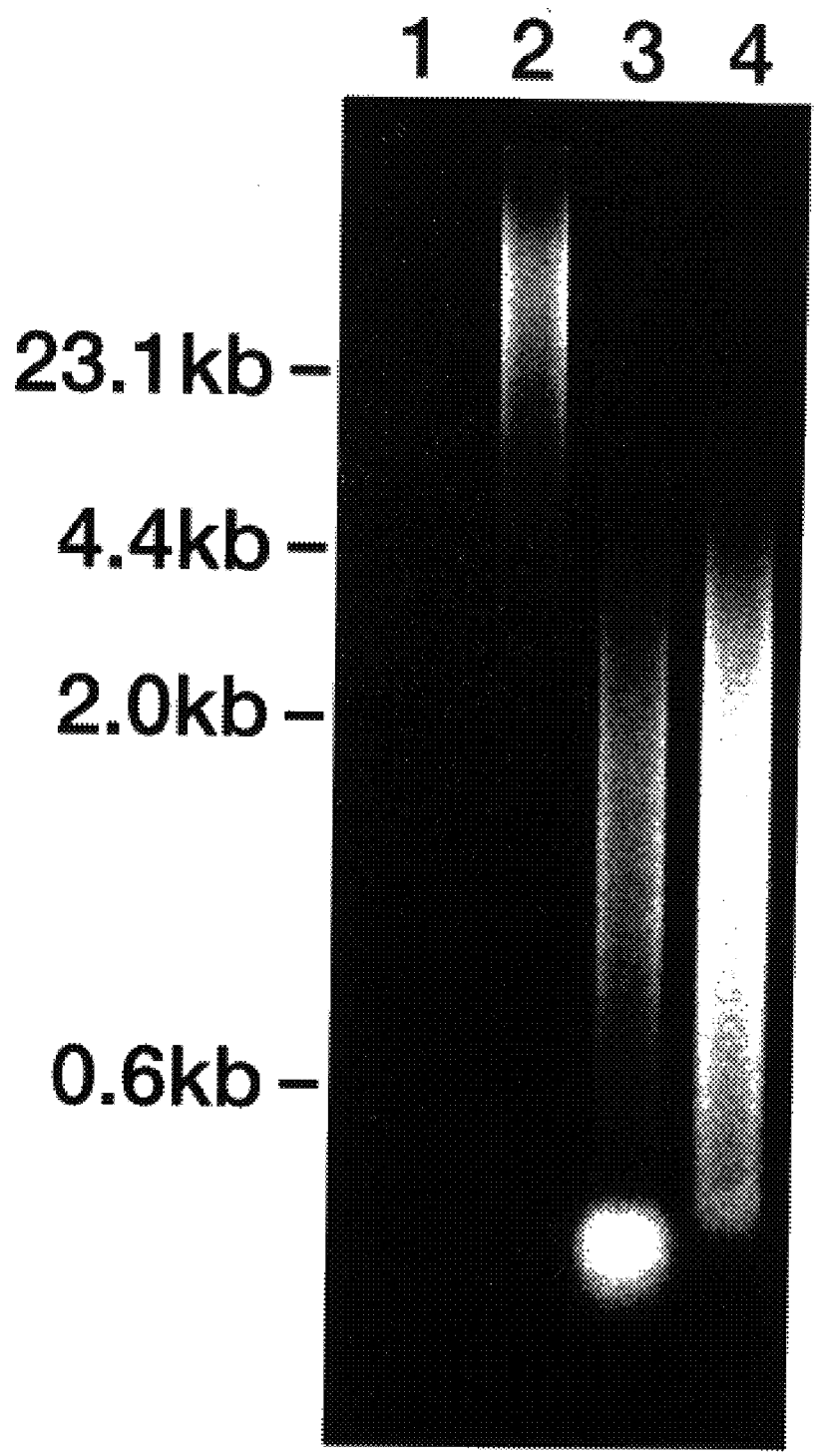
FIG. 3 is a photographic representation of the results of agarose gel electrophoresis illustrating ntp-DNA synthesis by various species of DNA polymerase as described in Example 4. Line 1—*Escherichia coli*—derived DNA polymerase I (DNA polymerase I); line 2—*Thermococcus litoralis*—derived DNA polymerase (Tli DNA polymerase); line 3—*Thermus thermophilous*—derived DNA polymerase (Tth DNA polymerase); and line 4—*Thermus aguaticus*—derived DNA polymerase (Tag DNA polymerase).

Then, the inventors examined, in this non-template and primer-dependent DNA synthesis reaction, the specificity of the deoxyribonucleotide triphosphates, which serve as substrates, namely the substrate specificity of said reaction. Samples consisting of one of the four deoxyribonucleotide triphosphates (A, T, G, C) or a combination of 2, 3 or 4 of the deoxyribonucleotide triphosphates were prepared and submitted to the ordinary reaction. A portion of each reaction mixture was subjected to agarose (1%) gel electrophoresis, followed by ethidium bromide staining. As shown in FIG. 2, DNA bands were confirmed for the reaction mixtures with the three deoxyribonucleotides dATP, dCTP and dTTP, or dATP, dGTP and dTTP added as well as for the reaction mixture with the four deoxyribonucleotides added. However, the reaction using all the four deoxyribonucleotide triphosphates and the reactions using said two combinations of three species gave results different in DNA band distribution. Thus, in the former case, DNA showed a size distribution within the range of about 1 kbp to 30 kbp while, in the latter case, DNA sizes were found distributed in the range above about 10 kbp and DNA larger in size were hardly observed. Thus, it was suggested that the products of such non-template and primer-dependent DNA synthesis should be of a different nature. In other words, the possibility that this non-template and primer-dependent DNA synthesis should involve a plurality of different reactions was suggested.

Then, the inventors prepared the DNA on a large scale for preparing a material for the characterization of the DNA obtained by the non-template and primer-dependent synthesis according to the present invention (hereinafter also referred to as "ntp-DNA"). For DNA purification, a cesium chloride-ethidium bromide equilibrium density-gradient centrifugation method [Sambrook et al., Molecular Cloning (A Laboratory Manual), Cold Spring Harbor Laboratory Press, 1989] was used. As a result, 9.5 mg of DNA was recovered from 475 ml of the reaction mixture.

Figure 7:
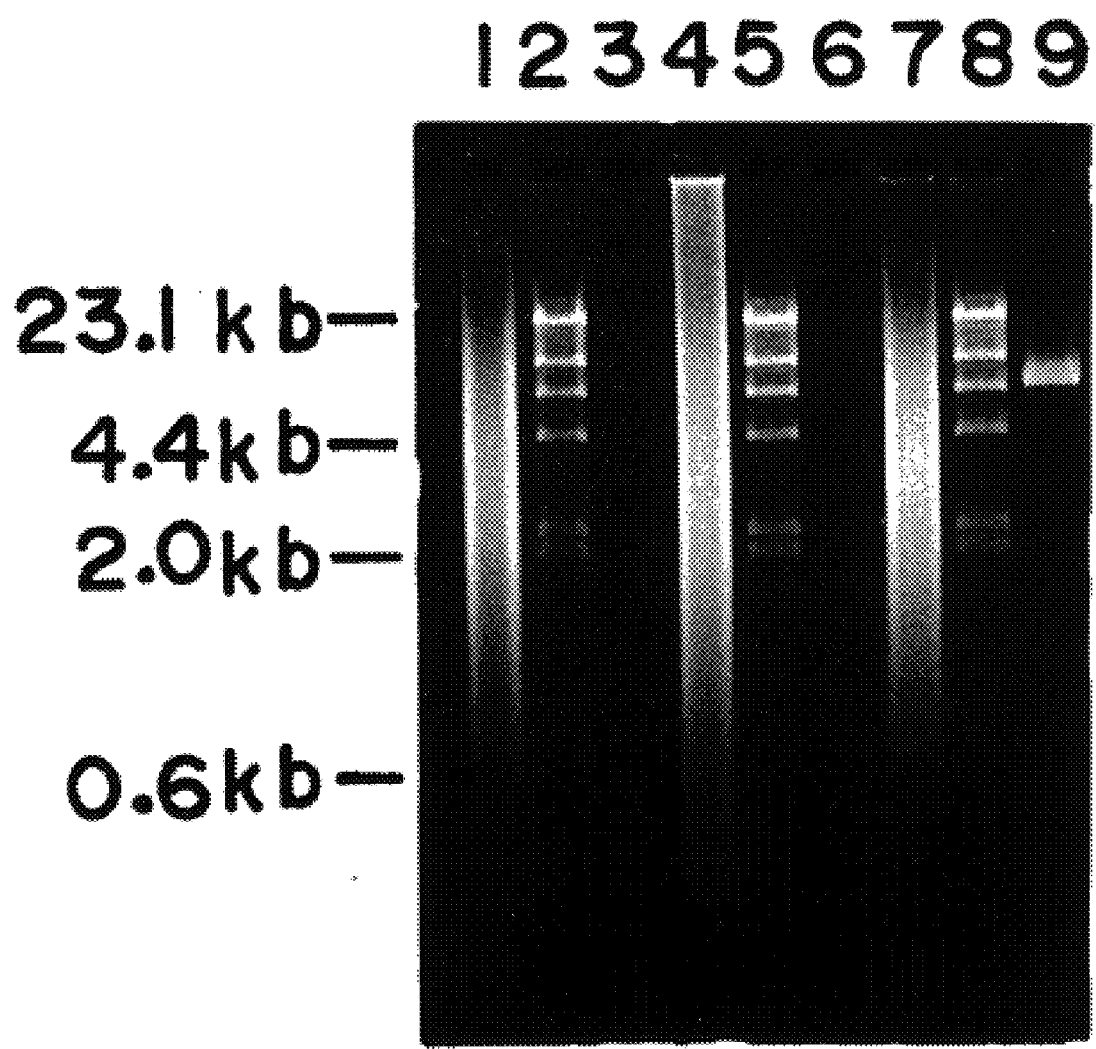
FIG. 7 is a photographic representation of the results of agarose gel electrophoresis, which indicates the cleavage of ntp-DNA with single-strand-specific nucleases as mentioned in Example 9. Line 1—S1 nuclease-treated ntp-DNA; line 2—S1 nuclease-treated λ/HindIII; line 3—S1 nuclease-treated M13mp18 single-stranded DNA; line 4—mung bean nuclease-treated ntp-DNA; line 5—mung bean nuclease-treated λ/HindIII; line 6—mung bean nuclease-treated M13mp18 single-stranded DNA; line 7, 8 and 9—ntp-DNA, λ/HindIII and M13mp18 single-stranded DNA, respectively, not treated with any single-strand-specific nuclease.

Using the sample thus prepared, the product of this non-template and primer-dependent synthesis (ntp-DNA) was cleaved with a single-strand-specific DNA nuclease, namely SI nucleasae or mung bean nuclease, to determine whether said product was single-stranded or double-stranded. As shown in FIG. 7, the ntp-DNA could not be cleaved with these single-strand-specific DNA nucleases, whereby the possibility of said ntp-DNA being a double-stranded DNA was suggested.

Figure 8:
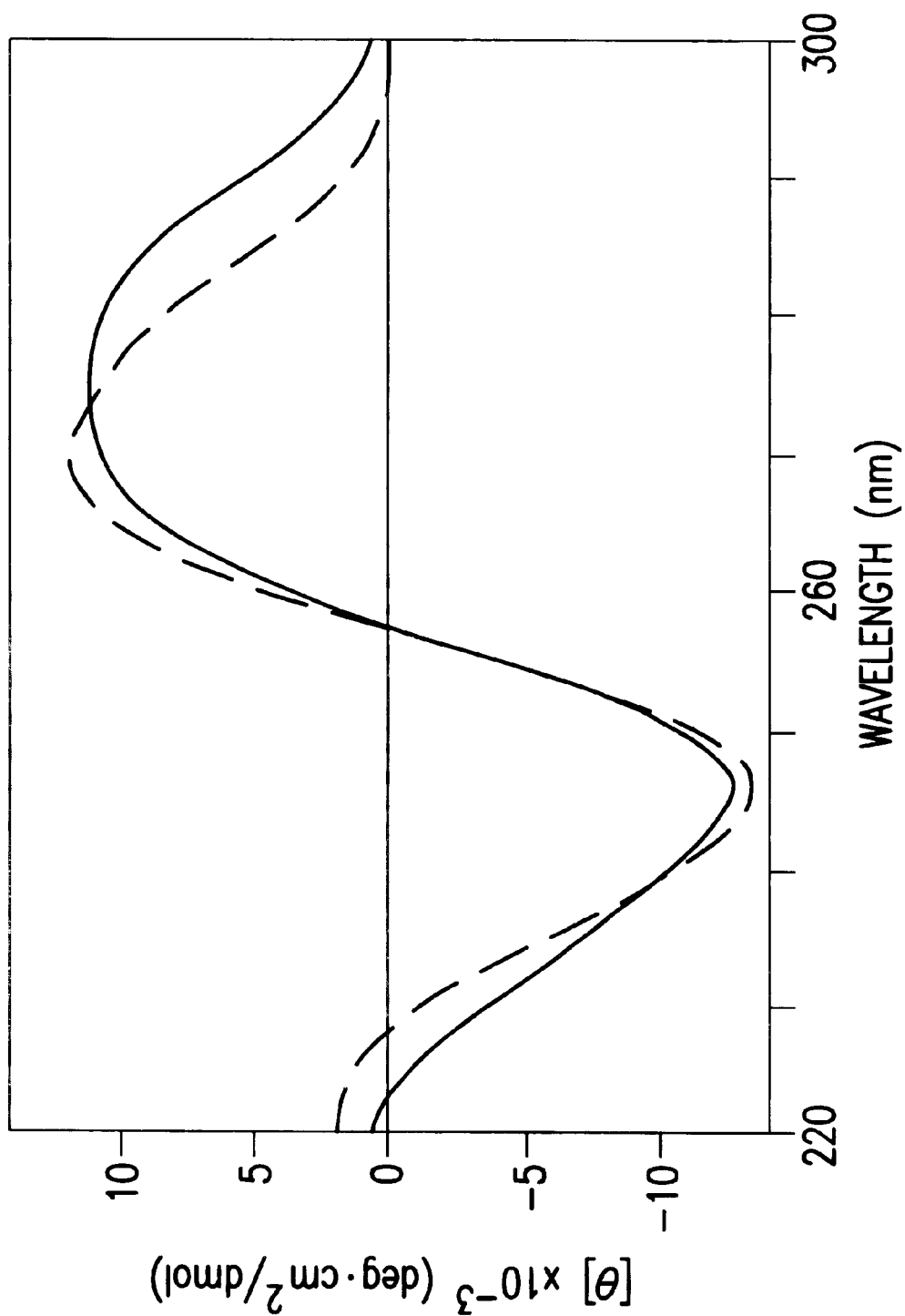
FIG. 8 is a circular dichroism spectrogram of ntp-DNA as referred to in Example 10. The solid line denotes pPT1/EcoRI and the broken line denotes the ntp-DNA.
Figure 9:
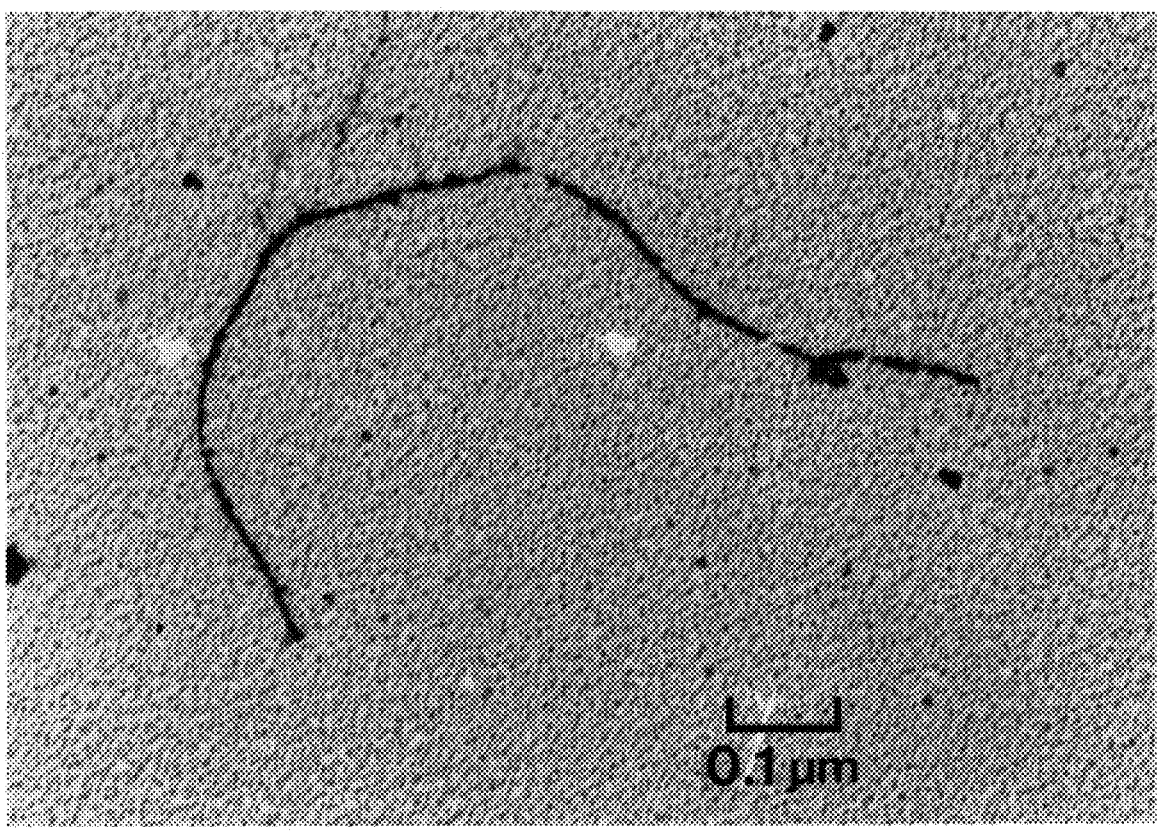
FIG. 9 is an electron photomicrograph of ntp-DNA as mentioned in Example 11.

Then, for studying the structure of said ntp-DNA, the inventors made observations by circular dichroism spectrometry and by means of a transmission electron microscopy. First, as regards the circular dichroism spectrometry, the data were substantially similar to those of typical type B double-helix DNA derived from a plasmid DNA, which was used as a control, by linearization with a restriction enzyme, as shown in FIG. 8. It was thus confirmed that said ntp-DNA is a DNA having the type B double-helix structure. Then, the transmission electron microscope observation confirmed, as shown in FIG. 9, that it is a linear DNA and is double-stranded as indicated by its diameter. Based on these analyses, the present inventors concluded that said ntp-DNA is double-stranded linear DNA.

Then, the inventors analyzed the base composition of the ntp-DNA. First, the ntp-DNA was cleaved (hydrolyzed) with deoxyribonuclease I and phosphodiesterase I as well as alkaline phosphatase to give various deoxyribonucleosides. The deoxyribonucleosides were quantitated by chromatography (high-performance liquid chromatography; Nihon Bunko chromatograph) on a Cosmosil 5C$_{18}$ reversed phase column (Nacalai Tesque). As a result, the base composition was found, as shown below in Table 1, to be as follows: 34.4% deoxyadenosine, 15.6% deoxycytosine, 17.4% deoxyguanine and 32.6% deoxythymidine; hence, the GC content was 33%.

TABLE 1

| Deoxynucleotide | Composition (%) |
|---|---|
| dA | 34.4 |
| dC | 15.6 |
| dG | 17.4 |
| dT | 32.6 |

Then, the inventors subjected the ntp-DNA to nearest neighbor base frequency analysis. An [α-$^{32}$P]-labeled deoxyribonucleotide triphosphate was added to an ordinary reaction mixture and the ordinary reaction was carried out. This reaction mixture was submitted to a Superlose 12 gel filtration column (Pharmacia) and a DNA solution was collected from a DNA peak. The DNA was purified by ethanol precipitation and dissolved in TE buffer. This labeled DNA was cleaved with Micrococcus nuclease and pancreatic phosphodiesterase to give deoxyribonucleoside 3'-monophosphates, followed by submission to a Cosmosil 5C$_{18}$ reversed phase column. Peaks of deoxyadenosine 3'-monophosphate (dAp), deoxycytidine 3'-monophosphate (dCp), deoxyguanosine 3'-monophosphate (dGp) and deoxythymidine 3'-monophosphate (dTp) were recovered. Thereafter, the $^{32}$P radioactivity of each peak was measured using a liquid scintillation counter (Beckman) for nearest neighbor base frequency analysis. As a result, a sequence with certain regularity was obtained, as shown in Table 2. Thus, dT and dG appeared with great frequency before dA, dT appeared with great frequency before dC, dA appeared with great frequency before dG, and dA and dC appeared with great frequency before dT. From these results, it was established that there are inclinations in the sequence of the ntp-DNA.

TABLE 2

| α-$^{32}$P-labeled deoxyribo- nucleotide triphosphate | Radioactivity of deoxyribo- nucleoside 3'-monophosphate | | | | | | | |
|---|---|---|---|---|---|---|---|---|
| | dAp | | dCp | | dGp | | dTp | |
| | pmol | % | pmol | % | pmol | % | pmol | % |
| dATP | 0 | 0 | 1.3 | 1.5 | 17.3 | 19.3 | 71.0 | 79.2 |
| dCTP | 0 | 0 | 0 | 0 | 2.7 | 10.8 | 22.2 | 89.2 |
| dGTP | 17.0 | 97.1 | 0 | 0 | 0.2 | 1.1 | 0.3 | 1.7 |
| dTTP | 34.0 | 44.2 | 40.5 | 52.6 | 2.5 | 3.2 | 0 | 0 |

Then, the inventors subjected this ntp-DNA to molecular cloning. The cloning vector used was pUC19 cleaved with the restriction enzyme SmaI (Toyobo). The insert DNA used was the ntp-DNA cleaved with DNase I so that it acquired flush (blunt) ends, dephosphorylated by treatment with alkaline phosphatase (Takara Shuzo), then again phosphorylated using T4 polynucleotide kinase (Toyobo) and finally repaired with the Klenow fragment. This insert DNA was ligated with the linearized cloning vector mentioned above and, for confirmation, the cloned plasmid was cleaved with restriction endonuclease to check electrophoretically whether the insert DNA was present or absent. As a result, clones with the desired DNA fragment inserted therein could be selected. The present inventors named them plasmids pTL34, pTL57 and pTL85.

Then, the inventors determined the base sequence of the insert DNA portion of each of the plasmids pTL34, pTL57 and pTL85. The base sequences could be determined by the dideoxy termination method [Sanger et al., Proc. Natl. Acad. Sci. USA, volume 74, pages 5463–5467 (1977)]. The base sequences determined are shown under SEQ ID NO:1, 2 and 3 is The Sequence Listing.

Then, the inventors checked whether this DNA was homologous to existing DNA. The results are shown in Table 3, Table 4 and Table 5 (in the same order as above). From these data, it is evident that this DNA sequence is conserved in chromosomes of a number of living organisms, including those of human. Interestingly enough, it is evident that this sequence is contained in gene regulatory regions such as microsatellite DNA occurring in the vicinity of the centromere.

TABLE 3

| Access NO. | Clone species | Homology (%) |
|---|---|---|
| X90770 | L. esculentum microsatellite DNA | 83.0 |
| L16355 | Human chromosome 10 | 80.0 |
| X92189 | D. polychroa microsatellite DNA | 79.6 |
| X78915 | D. melanogaster GATA12 repeat sequence | 79.6 |
| L19324 | Xenopus laevis recombinant active gene | 77.8 |
| Z68892 | B. vulgaris microsatellite DNA | 77.8 |

TABLE 4

| Access NO. | Clone species | Homology (%) |
|---|---|---|
| L13120 | Human repeat sequence | 84.8 |
| X90937 | L. esculentum microsatellite DNA | 89.7 |
| X78912 | D. melanogaster GATA5 repeat sequence | 84.8 |
| K00797 | Rat repeat sequence | 84.8 |
| X92189 | D. palychroa microsatellite DNA | 89.7 |

TABLE 5

| Access NO. | Clone species | Homology (%) |
|---|---|---|
| L13122 | Human repeat sequence | 79.4 |
| M35828 | Human BKm repeat sequence | 79.4 |
| Z33997 | Bovine microsatellite DNA | 79.4 |
| K01665 | D. melanogaster Bkm DNA | 82.4 |
| X90770 | L. esculentum microsatellite DNA | 76.5 |

Then, to check whether or not said ntp-DNA could serve as a probe for searching for DNA having a base sequence homologous or similar to that of this DNA among a tomato chromosome library, for instance, the inventors prepared a probe for such searching by labeling the 5'-terminal phosphate residue of this ntp-DNA with [γ-$^{32}$P]ATP, for instance. Any of various fluorescence-labeled probes may also be used as the labeled probe. As a result of screening of a tomato chromosome cDNA λ phage library by plaque hybridization using said probe, a number of positive signals were detected. The λ phage was isolated from each plaque identified by such positive signal and subjected to base sequencing. As expected, it was confirmed that the sequence of the ntp-DNA was contained therein. From this finding, it could be established that the ntp-DNA can serve as a probe for screening homologous or similar sequences occurring in various cDNA libraries.

Then, the inventors performed the following experiment in an attempt to confirm that the ntp-DNA had high frequency recombination activity. For the gene manipulation of the yeast used in the experiment, the method of Rose et al [Methods in Yeast Genetics (A Laboratory Course Manual), Cold Spring Harbor Laboratory Press, (1990)] was employed.

First, the βgalactosidase gene was amplified from the plasmid pCH110 (Pharmacia) by the PCR method. On that occasion, the GAL1 promoter sequence of baker's yeast (Saccharomyces cerevisiae) was added to the 5' terminus side of the upstream primer and the antisense sequence of the transcription termination signal CYC1 of baker's yeast was added to the 5' terminus side of the downstream primer, each in the correct reading frame with respect to the β-galactosidase gene codons. This procedure allows expression of the β-galactosidase gene within the yeast. Then, an ntp-DNA was synthesized at the 3' OH end of the double-stranded DNA containing said β-galactosidase gene using, for instance, Thermococcus litoralis DNA polymerase. In lieu of this procedure, the ntp-DNA may be joined to both ends of the β-galactosidase gene using DNA ligase. Thereafter, the resultant DNA was used to transfect baker's yeast, and yeast cells were cultured on a plate medium. Yeast colonies were respectively isolated from this plate, further cultured and submitted to a β-galactosidase activity assay. The β-galactosidase activity, if confirmed, would mean the expression of β-galactosidase originally absent in the yeast. The DNA used for transfection has no yeast replication origin, and hence cannot replicate in yeast cells. Therefore, β-galactosidase in yeast cells must be considered to be the result of expression thereof following integration of said gene into the yeast chromosome. As a result of β-galactosidase activity assay of yeasts, the β-galactosidase activity could indeed be detected. Hence integration of the gene into the yeast chromosome was confirmed (Table 6). These findings proved that said ntp-DNA is capable of causing recombination with great frequency, enabling protein expression from the inserted gene without requiring any special expression vector. The present invention has thus made it possible to effect expression of any desired protein without requiring such a troublesome procedure as expression vector construction. This method can also be applied to living organisms other than yeasts, for example Escherichia coli and other prokaryotic organisms as well as eukaryotic organisms.

TABLE 6

| Sample No. | β-galactosidase activity nmol/min/mg protein |
|---|---|
| 1 | 0.5 |
| 2 | 0.4 |
| 3 | 304 |
| 4 | 0.6 |
| 5 | 0.5 |
| 6 | 1.0 |
| 7 | 0.5 |
| 8 | 207 |
| 9 | 0.8 |
| 10 | 335 |
| 11 | 0.3 |
| 12 | 0.5 |
| 13 | 0.3 |
| 14 | 0.6 |
| 15 | 0.2 |
| 16 | 0.5 |
| 17 | 0.7 |
| 18 | 256 |
| 19 | 0.2 |
| 20 | 0.3 |

The present invention was completed based on a number of novel discoveries, including the finding mentioned above. It relates to a method of synthesizing DNA which comprises polymerizing deoxyribonucleotides in the absence of a template and primers and in the presence of a protein, polydeoxynucleotides synthesized by the method, a method of creating novel DNA by culturing cells transfected with the DNA mentioned above, said the novel DNA and a use thereof.

The method of npt-DNA synthesis according to the present invention is carried out in the absence of a template and primers and in the presence of a protein, as mentioned above. While the polymerization reaction proceeds in the presence of DNA polymerase, the polymerase itself or a protein other than polymerase may be used as the protein.

Preferred DNA polymerase species are those resistant to inactivation even at temperatures exceeding about 20° C., preferably exceeding about 60° C., and more preferably exceeding about 70° C. As examples of such species, there may be mentioned DNA polymerase species derived from bacterial strains belonging to the genus Thermococcus, such as the above-mentioned Thermococcus litoralis-derived DNA polymerase [Vent DNA polymerase (trademark), New England Biolabs], Thermococcus profundus (ATCC 51592)-derived DNA polymerase, Thermococcus stetteri-derived DNA polymerase and Thermococcus peptonophilus-derived DNA polymerase.

As DNA polymerase species derived from bacterial strains belonging to the genus Thermus, there may be mentioned Thermus aquaticus-derived DNA polymerase, Thermus thermophilus-derived DNA polymerase [Ampli Taq DNA polymerase (trademark), Perkin Elmer], [Tth DNA polymerase (trademark), Promega], Thermus flavus-derived DNA polymerase [Tfl DNA polymerase (trademark), Promega], Thermus flavus-derived DNA polymerase [Tfl DNA polymerase (trademark), Promega], Thermus lacteus (ATCC 31557)-derived DNA polymerase Thermus rubens (ATCC 31556)-derived DNA polymerase, Thermus ruber (ATCC 51134)-derived DNA polymerase, Thermus filiformis (ATCC 43280)-derived DNA polymerase and Thermus scotoductus (ATCC 27978)-derived DNA polymerase.

The DNA polymerase species mentioned above may be used either singly or combinedly in a mixed system containing two or more (two, three, . . . ) of them. When the deoxyribonucleotide polymerization is carried out using two or more DNA polymerase species combinedly, a larger variety of DNA are obtained simultaneously (namely a group of DNA more diversified in base sequences is obtained) as compared with the case of polymerization with only one DNA polymerase species. This leads to an increased content of DNA capable of becoming chromosomal DNA on the occasion of chromosome synthesis.

dATP, dTTP, dGTP and dCTP are used as the deoxyribonucleotides. When three or four of them are present in the reaction system, the reaction proceeds.

The reaction of the deoxyribonucleotides and DNA polymerase is preferably carried out under weakly acidic conditions at a pH of about 6, under neutral conditions or under weakly alkaline conditions at pH 10 or below.

The reaction temperature and period can be selected within those ranges in which the polymerase will not be inactivated. The reaction proceeds rapidly when the reaction temperature is selected within the range not lower than about 20° C., preferably not lower than about 60° C., but compatible with the polymerase activity, and the reaction is carried out for about 0.5 to 24 hours, preferably 1 to 15 hours, and more preferably 2 to 10 hours. For instance, the reaction may be conducted at 74° C. for several hours, or the ordinary PCR conditions may be employed, for example the cycle according to the schedule: (1) 1 minute at 95° C., (2) 2 minutes at 45° C. and (3) 3 minutes at 74° C. may be repeated.

The reaction is initiated after a certain initial lag time and soon it attains the maximum rate. The ntp-DNA synthesized by the method of the present invention are thought to be the products of the synthesis not dependent on DNA or RNA which serve as the template and/or primer but dependent on the information of the protein (polymerase) used in the reaction.

The sizes of DNA synthesized are generally distributed in the range of 1 kbp to 30 kbp. The sizes can be varied by modifying the reaction conditions. For example, when all four of dATP, dGTP, dCTP and dTTP are used as substrates, DNA of 1 to 30 kbp can be obtained. When three of the four (one being omitted), for example dATP, dCTP and dTTP, are used as substrates, DNA of about 10 kbp can be obtained. When deoxyribonuclease I is added to a reaction system containing the four deoxyribonucleotides as substrates, DNA of about 10 kbp can be obtained.

The thus-obtained product ntp-DNA are double-stranded and, in an example (Example 12), their base composition is as follows: 34.4% deoxyadenine (dA), 15.6% deoxycytidine (dC), 17.4% deoxyguanine (dG) and 32.6% deoxythymidine (dT), the total of dG and dC being 33%. In the DNA base sequence in another Example (Example 14), the frequencies of the sequences dTdA, dTdC, dAdG, dAdT and dCdT are great (Example 13, Table 2).

Since the npt-DNA synthesized have a high frequency of recombination activity, they can be used to transfect prokaryotic organisms and eukaryotic organisms, such as yeasts and Escherichia coli, without using any expression vector, to express protein coaded by the npt-DNA.

The ntp-DNA can be labeled, for example with a radioactive isotope, a fluorescent dye (fluoresceine, biotin derivatives, umbelliferone, rhodamine B, eosin) or the like for their use as probes for screening DNA having a sequence homologous or similar to those of the ntp-DNA from human chromosome libraries, tomato chromosome libraries and other cDNA libraries. Such screening can be performed by per se known methods, for example using plaque hybridization and Southern blotting.

Furthermore, the present inventors surprisingly made the following findings. The DNA synthesized by the reaction mentioned above were found to contain, in their base sequences, those repetitive sequences comprising 8 or 12 bases and nonrepetitive sequences which are recognizable as the above-mentioned three regions essential to function as chromosomal DNA. Furthermore, when such chromosomal DNA were introduced into cells, the chromosomal DNA were found to readily bind to proteins such as histones (another essential chromosomal component) produced spontaneously within cells.

Therefore, it is possible to synthesize DNA either extracellularly or intracellularly using the abovementioned DNA polymerase and use the thus-synthesized DNA in allowing said chromosomal DNA to mature into chromosomes within cells.

Thus, when a double-stranded linear DNA having the three essential elements, namely the centromere, telomere and replication origin regions on the same molecule is synthesized extracellularly (e.g., in vitro) using DNA polymerase and then this DNA is introduced into cells, this integral DNA (chromosomal DNA) binds to proteins such as histones within cells and thus functions as a chromosome. Once it has succeeded in functioning as a chromosome, it is replicated once in synchronization with each occasion of cell division, so that each daughter cell is given one counterpart. It is also possible to cause intracellular production of DNA polymerase using an appropriate expression vector and cause this DNA polymerase to produce chromosomal DNA for conversion of the latter to chromosomes.

It is only some molecules of the group of novel DNA molecules synthesized by the intermediary of a protein, for example DNA polymerase, that function as chromosomal DNA. Other molecules of such group will not function as chromosomal DNA. When introduced into cells, such nonfunctional DNA will disappear (not remain) in the process of cell division. In other words, when a novel group of DNA molecules are synthesized introduced into cells and these cells are cultured and certain DNA remain after a certain number of times of cell division, those remaining DNA may be said to be equipped with elements needed for chromosomal DNA, hence they are able to function satisfactorily.

According to the present invention, chromosomes are produced by introducing DNA synthesized into cells, as mentioned above. As typical examples of the cells that can be used in that case, there may be human HeLa cells, human KB cells, human CAPAN-1 cells, murine L1210 cells, murine 3T3 cells, simian COS7 cells, human PANC-1 cells and the like. If, in this reaction, a desired gene, for example a drug resistance gene, is introduced into the reaction system in the double-stranded linear form, novel DNA are synthesized additionally on both ends of the gene DNA, which leads to the formation of an independent chromosome containing the desired gene. The desired gene thus can be converted to a "chromosome".

At present, methods are known for the production of those thermostable DNA polymerase species to be used in the practice of the present invention or for the purification of the genes coding for the same. Those skilled in the art would be able to carry out such methods with ease. Relevant patent documents are as follows: JP-A-02060585, JP-B-08024570 (JP-A-02000434), JP-A-05068547, JP-B-07059195 (JP-A-05130871), JP-A-05328969, JP-A-07051061, JP-A-06339373, JP-A-06007160, etc.

As mentioned hereinabove, the present invention has an object to creatively produce DNA, namely pieces of genetic information, by means of DNA polymerase in a non-template and primer-dependent manner. The DNA thus created perform important functions in the field of genetic engineering. It is possible to create DNA not occurring in the natural world, hence to create chromosomes and, further, to create proteins based on these genes. Therefore, it is possible to create, for example, non-naturally-occurring physiologically active substances, enzymes, receptors, signal transmitters or transducers, hormones, anticancer substances, antiviral substances, immunosuppressant substances, membrane transport proteins, development-related substances, cytoskeletal substances, cranial nerve-related substances, etc. Furthermore, through this DNA creation, it is possible to peep, though fragmentarily, into the creation of genetic information in the process of organic evolution. There is the possibility of reproducing the same and, as a matter of course, producing useful mutants. Further, for instance, the repeat sequence DNA presumably occurring partly in the constituent elements of such created DNA have the utility in elucidating the mechanisms of regulation of gene replication, transcription, expression and so on, or as probes for screening regulatory sites of existing genes. Another utility lies in that by adding the ntp-DNA terminally to an existing gene, followed by introduction into host cells, homologous recombination with the host chromosome can be caused to occur with great frequency to thereby cause expression of the protein originating from the gene. The present invention expectedly plays an important role in the field of genetic engineering in the future, since it can be practiced in an easy and simple manner and at low cost, and it requires no particular apparatus.

Furthermore, the present invention makes it possible to readily synthesize double-stranded linear DNA having the centromere, telomere and replication origin regions integrated therein and to readily produce chromosomes by using the chromosomal DNA obtained.

PREFERRED EMBODIMENTS OF THE INVENTION

The present invention is now described in terms of the following examples, which are by no means limited to the scope of the present invention.

EXAMPLE 1

(ntp-DNA synthesis using *Thermococcus litoralis* DNA polymerase [Vent DNA polymerase (trademark), New England Biolabs]

To a reaction mixture (100 µl) comprising buffer A [10 mM KCl, 10 mM $(NH_4)_2SO_4$, 20 mM Tris/HCl (pH 8.8), 6 mM $MgCl_2$, 0.1% Triton X-100 (all in final concentration)], deoxyribonucleotides [dATP, dCTP, dGTP and dTTP (all in final concentration 200 µM)] and 20 units/ml *Thermococcus litoralis* DNA polymerase was added an equal volume of mineral oil (Sigma), and the reaction was allowed to proceed at 74° C. for 3 hours. Then, 20 µl of the reaction mixture was applied to 1% agarose, Tris/acetic acid/EDTA gel [Sambrook, T. et al. Molecular Cloning (A Laboratory Manual), Cold Spring Harbor Laboratory Press, published 1989] and, after electrophoresis, staining was performed with 0.5 µg/ml ethidium bromide, followed by photography. DNA bands stained in the wide range of about 1 kbp to 30 kbp are identified, as shown in FIG. 1.

EXAMPLE 2

(ntp-RNA synthesis using ribonucleotides and *Thermococcus litoralis* DNA polymerase)

To a reaction mixture (100 µl) comprising buffer A, ribonucleotides [ATP, CTP, GTP and TTP (all in final concentration 200 µM)] and 20 units/ml *Thermococcus litoralis* DNA polymerase was added an equal volume of mineral oil, and the reaction was allowed to proceed at 74° C. for 3 hours. Then, 20 µl of the reaction mixture was applied to 1% agarose, Tris/acetic acid/EDTA gel and, after electrophoresis, staining was performed with 0.5 µg/ml ethidium bromide, followed by photography. No stained RNA bands appeared, hence it was concluded that ribonucleotides cannot serve as substrates in this non-template and primer-dependent synthesis reaction.

EXAMPLE 3

(Photography of deoxyribonucleotides in ntp-DNA synthesis using *Thermococcus litoralis* DNA polymerase)

To a reaction mixture (100 µl) comprising buffer A, deoxyribonucleotides [one, two, three or four of dATP, dATP, dCTP, dGTP and dTTP (all in final concentration 200 µM)] and 20 units/ml *Thermococcus litoralis* DNA polymerase was added an equal volume of mineral oil, and the reaction was allowed to proceed at 74° C. for 3 hours. Then, 10 µl of the reaction mixture was applied to 1% agarose, Tris/acetic acid/EDTA gel and, after electrophoresis, staining was performed with 0.5 µg/ml ethidium bromide, followed by photography. As shown in FIG. 2, when all the four deoxyribonucleotides or the three dATP, dGTP and dTTP or the three dATP, dCTP and dTTP were used, ntp-DNA bands were observed. When one or two of the deoxyribonucleotides or the other combination of three were used, no ntp-DNA bands were observed. It was thus established that, in this ntp-DNA synthesis reaction, there is specificity to deoxyribonucleotide triphosphates to serve as substrates (namely substrate specificity of this reaction). Furthermore, in the reaction conducted with all the four deoxyribonucleotide triphosphates added, the sizes of the DNA synthesized were found distributed in the range of about 1 kbp to 30 kbp whereas, in the reaction conducted using three deoxyribonucleotide triphosphates, said sized were distributed in the range above about 10 kbp, with DNA of larger sizes being hardly observed. This difference in DNA band distribution suggested the possibility that these products of ntp-DNA synthesis might differ in kind. In other words, the possibility was suggested that this non-template and primer-dependent DNA synthesis might involve a plurality of different reactions.

EXAMPLE 4
(ntp-DNA synthesis using different DNA polymerase species)

To a reaction mixture (100 μl) comprising buffer A, deoxyribonucleotides [dATP, dCTP, dGTP and dTTP (all in final concentration 200 μM)] and one of different DNA polymerase species [20 units/ml *Thermococcus litoralis* DNA polymerase or 50 units/ml *Thermus aquaticus* DNA polymerase or 40 units/ml *Thermus thermophilus* DNA polymerase (all in final concentration)] was added an equal volume of mineral oil, and the reaction was allowed to proceed at 74° C. for 3 hours. Separately, to a reaction mixture (100 μl) comprising buffer B [60 mM phosphate buffer (pH 7.4), 6 mM MgCl$_2$], deoxyribonucleotides [300 μM dATP, 300 μM dTTP, 1.5 mM dGTP and 1.5 mM dCTP (all in final concentration)] and 2.5 units/ml *Escherichia coli* DNA polymerase I was added an equal volume of mineral oil, and the reaction was allowed to proceed at 37° C. for 3 hours. Thereafter, 10 μl of each reaction mixture was applied to 1% agarose, Tris/acetic acid/EDTA gel and, after electrophoresis, staining was performed with 0.5 μg/ml ethidium bromide, followed by photography. When the DNA polymerase species from the thermophilic prokaryotic bacterial species *Thermus aquaticus* and *Thermus thermophilus* were used, DNA bands of several bp to 10 kbp and DNA bands of several bp to 7 kbp were found, respectively. On the other hand, with the DNA polymerase species from *Escherichia coli*, which is also a prokaryotic organism, no DNA bands were observed. These results indicated that the non-template and primer-dependent synthesis reaction depends largely on the polymerase species. It was also established that the non-template and primer-dependent synthesis reaction can take place even with DNA polymerase species other than *Thermococcus litoralis* DNA polymerase, hence the reaction is a fairly universal phenomenon.

EXAMPLE 5
(Checking the presence or absence of DNA or RNAs as possible contaminants in enzymes for use in ntp-DNA synthesis reaction)

Figure 4:
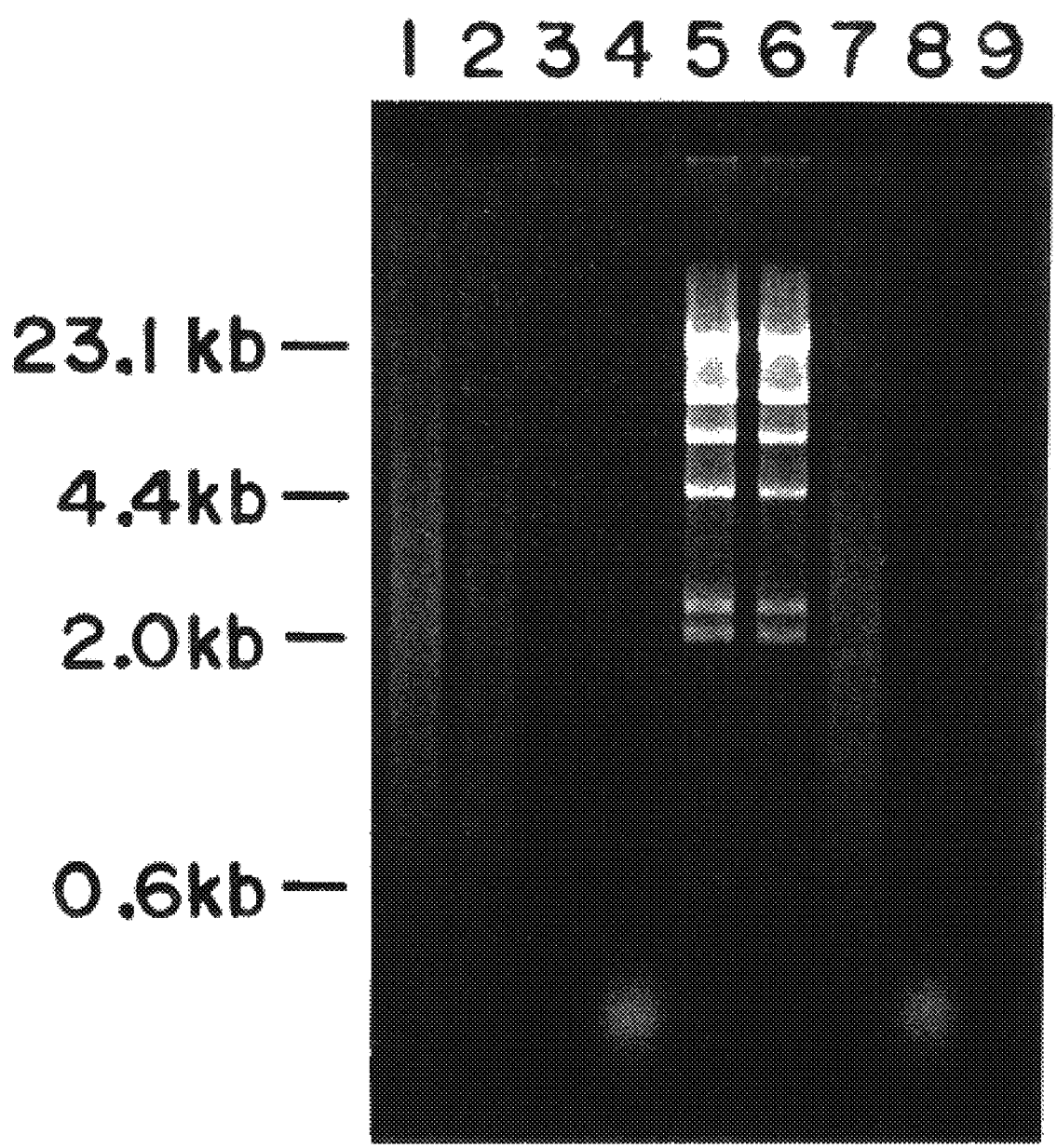
FIG. 4 is a photographic representation of the results of agarose gel electrophoresis to determine whether contaminant DNA and/or RNAs were present in the enzyme shown in Example 5. Line 1—ordinary ntp-DNA synthesis; line 2—Tli DNA polymerase pretreated with RNase A; line 3—tRNA treated with RNase A; line 4—tRNA not treated with RNase A; line 5—λ/HindIII treated with RNase A; line 6—λ/HindIII not treated with RNase A; line 7—Tli DNA polymerase pretreated with DNase I: line 8—tRNA treated with DNase I; and line 9—λ/HindIII treated with DNase I.

To a reaction mixture (92 μl) comprising buffer A, 1 μg/ml ribonuclease A (RNase A, Worthington) or 1.25 μg/ml deoxyribonuclease I (DNase I, Boehringer Mannheim Biochemicals) and 20 units/ml *Thermococcus litoralis* DNA polymerase was added an equal volume of mineral oil, and the reaction was allowed to proceed at 37° C. for 2 hours. Then, 8 μl of 2.5 mM deoxyribonucleotides [dATP, dCTP, dGTP and dTTP (all in final concentration 200 μM)] was added and the reaction was allowed to proceed at 74° C. for 3 hours. Thereafter, 1 μl of 500 mM EDTA was added to 20 μl of the reaction mixture, the whole mixture was applied to 1% agarose, Tris/acetic acid/EDTA gel and, after electrophoresis, staining was performed with 0.5 μg/ml ethidium bromide, which was followed by photography. Separately, in control runs for checking the positive reactions of the nucleases, a reaction mixture (92 μl) comprising buffer A, 1 μg/ml RNase A or 1.25 μg/ml DNase I, and 0.3 mg/ml transfer RNAs (tRNAs; Sigma) or 30 μg/ml HindIII-cleaved λ DNA (λ/HindIII; Toyobo) was prepared and the same reaction and electrophoresis as mentioned above were performed. It was established that RNase A and DNase I can indeed cleave RNA and DNA, respectively, in said buffer, as shown in FIG. 4. Since the non-template and primer-dependent synthesis took place even after treatment of the reaction mixture with RNase A and DNase I which degrade contaminant RNAs and DNA (if ever present), it was concluded with certainty that the reaction does not require any RNA or DNA primers.

EXAMPLE 6
(Synthesis of 10 kbp ntp-DNA using *Thermococcus litoralis* DNA polymerase)

To a reaction mixture (100 μl) comprising buffer A, 1.25 μg/ml DNase I, deoxyribonucleotides [dATP, dCTP, dGTP and dTTP (all in final concentration 200 μM)] and 20 units/ml *Thermococcus litoralis* DNA polymerase was added an equal volume of mineral oil, and the reaction was allowed to proceed at 37° C. for 30 minutes and then at 74° C. for 3 hours. Then, 20 μl of the reaction mixture was applied to 1% agarose, Tris/acetic acid/EDTA gel and, after electrophoresis, staining was performed with 0.5 μg/ml ethidium bromide, followed by photography. As shown in FIG. 5, a dark band appeared in the vicinity of 10 kbp. This result indicates that the length of the product DNA can be varied arbitrarily by modifying the reaction conditions.

EXAMPLE 7
(Time course of ntp-DNA synthesis reaction)

To a reaction mixture (50 μl) comprising buffer A, deoxyribonucleotides [dATP, dCTP, dGTP and dTTP (all in final concentration 200 μM)], [α-$^{32}$P]-labeled deoxyribonucleotides [dATP, dCTP, dGTP and dTTP (all in final concentration 100 nM, 3.3×10$^6$ Bq/pmol)] and 20 units/ml *Thermococcus litoralis* DNA polymerase was added an equal volume of mineral oil, and the reaction was allowed to proceed at 74° C. for 0, 1, 2, 3 or 4 hours. Then, the reaction was terminated by addition of 2 μl of 500 mM EDTA, 4 μl of the reaction mixture was added to 96 μl of 0.5 mg/ml calf thymus DNA, and the $^{32}$P radioactivity of the acid-insoluble fraction was measured using a liquid scintillation counter. As shown in FIG. 6, no deoxyribonucleotide incorporation was observed until hour 1 and, at hour 2, the incorporation was first observed. Then, until hour 4, about 9% of the deoxyribonucleotides added were incorporated. Based on the data for the reaction period from hour 1 to hour 2, the maximum rate of reaction was calculated to be 0.88 base incorporation per protein molecule per second. This is one 76th as compared with the ordinary template- and primer-dependent DNA polymerization reaction in the presence of *Thermococcus litoralis* DNA polymerase and one 57th as compared with the corresponding reaction in the presence of *Escherichia coli* DNA polymerase I, suggesting that said non-template and primer-dependent reaction is quite different from the ordinary template- and primer-dependent DNA polymerization reaction.

EXAMPLE 8
(Purification of product of ntp-DNA synthesis)

To a reaction mixture (475 ml) comprising buffer A, deoxyribonucleotides [dATP, dCTP, dGTP and dTTP (all in final concentration 200 μM)] and 20 units/ml *Thermococcus litoralis* DNA polymerase was added an equal volume of mineral oil, and the reaction was allowed to proceed at 74° C. for 3 hours. Then, chloroform was added in an amount equal to that of mineral oil, the resultant mixture was centrifuged (17,700×g, 2 minutes), and the upper layer solution was transferred to a separate vessel. After removal, by this procedure, of the mineral oil from the reaction mixture, one-tenth volume of 3 M sodium acetate and 2.5 volumes of ethanol were added, and the mixture was stored at −85° C for 2 hours and then centrifuged. The DNA fraction thus recovered was dissolved in 5 ml of TE buffer [10 mM Tris/HCl (pH 8.0), 1 mM EDTA]. This roughly purified DNA solution was purified by the cesium chloride-ethidium bromide equilibrium density gradient centrifugation method [Sambrook et al., Molecular Cloning (A Laboratory Manual), Cold Spring Harbor Laboratory Press, published 1989]. As a result, 9.5 mg of ntp-DNA was obtained.

EXAMPLE 9
(Cleavage of ntp-DNA with single-stranded DNA-specific nuclease)

A reaction mixture (10 μl) comprising S1 buffer [50 mM acetic acid/NaOH (pH 5.0), 30 mM NaCl, 1 mM $ZnSO_4$, 26 units/ml S1 nuclease (Takara Shuzo)] or MB buffer [30 mM acetic acid/NaOH (pH 4.6), 280 mM NaCl, 1 mM $ZnSO_4$, 43 units/ml mung bean nuclease (Toyobo)], and 58.5 μg/ml ntp-DNA or 20 μg/ml M13mp18 single-stranded DNA was incubated at 37° C. for 5 minutes to thereby allow the reaction to proceed. Thereafter, 1 μl of 500 mM EDTA was added to terminate the reaction, the mixture was applied to 1% agarose, Tris/acetic acid/EDTA gel and, after electrophoresis, staining was performed with 0.5 μg/ml ethidium bromide, followed by photography. As shown in FIG. 7, the single-stranded DNA was cleaved and the band disappeared whereas the ntp-DNA after the reaction did not show any change as compared with that before the reaction, that is, ntp-DNA was not cleaved with those nucleases. This suggested the possibility that the ntp-DNA was not single-stranded, but some other DNA species, for example, a double-stranded one.

EXAMPLE 10
(Analysis, based on circular dichroism, of DNA double helix structure of ntp-DNA)

In 0.5 ml of TE buffer [10 mM Tris/HCl (pH 8.0), 1 mM EDTA] was dissolved 700 μg of the ntp-DNA prepared in Example 8, and the solution was subjected to circular dichroism spectroscopy at room temperature using a Nippon Bunko model J-500A circular dichroism dispersion meter. The ntp-DNA gave the spectrum shown in FIG. 8 (solid line) almost identical to the circular dichroism spectrum (broken line) of the linear pPT1 plasmid DNA, representative of typical double-stranded type B DNA, suggesting that there exists dextral helix of the same density per unit concentration of the ntp-DNA. Therefore, it was concluded that ntp-DNA is double-stranded type B DNA.

EXAMPLE 11
(Observation, by an electron microscope, of ntp-DNA)

Using 0.05 μg of the ntp-DNA prepared in Example 7, transmission electron microscopy was performed by the method disclosed by Sassenbach [Journal of Virology, volume 12, pages 1131–1138 (1973)]. It was confirmed that it is linear DNA, as illustrated in FIG. 9.

EXAMPLE 12
(Base composition of ntp-DNA)

A reaction mixture (20 μl) comprising buffer C [25 mM Tris/HCl (pH 8.0), 25 mM $MgCl_2$], 1.5 mg/ml ntp-DNA, 50 units/ml DNase I, 5 units/ml phosphodiesterase I and 2.3 units/ml alkaline phosphatase (Takara Shuzo) was incubated at 37° C. for 2 hours to allow the reaction to proceed. Then, the whole amount of the mixture was applied to a Cosmosil $5C_{18}$ (Nacalai Tesque) column (4 ml) equilibrated with PA solvent (10 mM sodium dihydrogen phosphate:acetonitrile=98:2), followed by elution with PA solvent. The amounts of deoxyadenine (dA), deoxycytidine (dC), deoxyguanine (dG) and deoxythymidine (dT) were determined based on the respective peak areas, followed by calculation of the base composition. As shown in Table 1, the results were as follows: 34.4% dA, 15.6% dC, 17.4% dG and 32.6% dT, the GC content being 33%.

EXAMPLE 13
(Nearest neighbor base frequency analysis of ntp-DNA)

To a reaction mixture (50 μl) comprising buffer A, deoxyribonucleotides [dATP, dCTP, dGTP and dTTP (all in final concentration 200 μM), [$\alpha$-$^{32}$P]-labeled deoxyribonucleotides [dATP, dCTP, dGTP and dTTP (all in final concentration 100 nM, 3.3×106 Bq/pmol)] and 20 units/ml *Thermococcus litoralis* DNA polymerase was added an equal volume of mineral oil, and the reaction was allowed to proceed at 74° C. for 3 hours. Then, 20 mM EDTA was added to terminate the reaction. Thereto was added phenol:chloroform (1:1), followed by centrifugation (17,700×g, 2 minutes). The upper layer solution (40 μl) was submitted to a Superlose 12 gel filtration column (24 ml; Pharmacia), elution being performed with TE buffer. To the eluate was added 3 μl of 550 μg/ml calf thymus DNA, 0.1 volume of 3 M sodium acetate and 2.5 volumes of ethanol were further added and, after mixing, the mixture was allowed to stand overnight at –85° C., followed by centrifugation (21,600×g, 40 minutes, 4° C.). The sediment was washed with 70% ethanol, then dried and dissolved in 20 μl of TE buffer. To this sample was added a reaction mixture (840 μl) comprising buffer MP [20 mM succinic acid/NaOH (pH 6.0), 10 mM $CaCl_2$, 19 units/ml Micrococcus nuclease, 0.5 unit/ml pancreatic phosphodiesterase (all in final concentration)], and the reaction was allowed to proceed at 37° C. for 3 hours. Thereafter, the whole amount of the mixture was applied to a Cosmosil $5C_{18}$ (Nacalai Tesque) column (4 ml), elution was performed with 50 mM calcium formate, and the peaks of deoxyadenosine 3'-monophosphate (dAp), deoxycytidine 3'-monophosphate (dCp), deoxyguanosine 3'-monophosphate (dGp) and deoxythymidine 3'-monophosphate (dTp) were recovered. The volume of each eluate was adjusted to 1.5 ml and 200 μl of each dilution was transferred to a Ready cap (Beckman) and, after drying, the radioactivity of $^{32}$P was measured using a liquid scintillation counter. There was found an inclination in base sequence, as shown in Table 2.

EXAMPLE 14
(Cloning of ntp-DNA)

A reaction mixture (0.5 ml) comprising buffer D [50 mM Tris/HCl (pH 7.6), 10 mM $MnCl_2$, 0.1 mg/ml bovine serum albumin (BSA)], 400 μg/ml ntp-DNA and 0.08 unit/ml DNase I was incubated at 15° C. for 20 minutes to thereby allow the reaction to proceed. Thereafter, 20 μl of 500 mM EDTA was added to terminate the reaction and then an equal volume of phenol:chloroform (1:1) was added. After mixing, the mixture was centrifued at 9,600×g for 5 minutes. The upper layer was transferred to a separate vessel. (The above procedure is referred to as "phenol treatment".) To this upper layer was added an equal volume of chloroform and, after mixing, centrifugation was performed in the same manner as mentioned above and the upper layer was transferred to a separate vessel. This upper layer was purified by the cesium chloride-ethidium bromide equilibrium density gradient centrifugation, and the DNA obtained was dissolved in 40 μl of TE buffer [10 mM Tis/HCl (pH 8.0), 1 mM EDTA] (hereinafter, ntp-DNA/DNase I).

The above-mentioned DNA was dephosphorylated. Thus, a reaction mixture (100 μl) comprising dephosphorylation buffer [50 mM Tris/HCl (pH 9.0), 10 mM $MgCl_2$], 60 μg/ml ntp-DNA/DNase I and 100 units/ml alkaline phosphatase (Takara Shuzo) was heated at 65° C. for 1 hour to allow the reaction to proceed. Phenol treatment was performed, 0.1 volume of 3 M sodium acetate was added to the mixture, and after mixing, 2.5 volumes of ethanol were added. The resultant mixture was allowed to stand overnight at –20° C. and then centrifuged (21,600×g, 30 minutes, 4° C.) (hereinafter this procedure is referred to as ethanol precipitation). The sediment was washed with 70% ethanol and, after drying, dissolved in 10 μl of TE buffer (hereinafter, dephosphorylated ntp-DNA/DNase I).

The above DNA was phosphorylated. Thus, a reaction mixture (40 μl) comprising phosphorylation buffer [50 mM imidazole/HCl (pH 6.4), 18 mM $MgCl_2$, 5 mM DTT], 6% polyethylene glycol #8000, 150 μM ATP, 120 μg/ml dephosphorylated ntp-DNA/DNase I and 1.5 units/μl T4 polynucleotide kinase (Toyobo) was incubated at 37° C. for 1 hour to allow the reaction to proceed. Thereafter, the DNA was purified by phenol treatment and ethanol precipitation and then dissolved in 10 μl of TE buffer (hereinafter, phosphorylated ntp-DNA/DNase I).

Since there was the possibility that the phosphorylated ntp-DNA/DNase I might have gap structures, single strand regions in some or other places of the double-stranded DNA, repairs were made using DNA polymerase. Thus, a reaction mixture (50 μl) comprising repair buffer [50 mM Tris/HCl (pH 7.5), 10 mM $MgSO_4$, 0.1 mM dithiothreitol, 50 μg/ml BSA], deoxyribonucleotides [dATP, dCTP, dGTP and dTTP (all in final concentration 25 μM)], 120 μg/ml phsphorylated ntp-DNA/DNase I and 166 units/ml Klenow fragment (Toyobo) was incubated at 25° C. for 15 minutes to allow the reaction to proceed. Then, the DNA was purified by phenol treatment and ethanol precipitation and dissolved in 10 μl of TE buffer (hereinafter, repaired ntp-DNA/DNase I).

Next, a cloning vector was prepared. Thus, a reaction mixture (200 μl) comprising SmaI buffer [10 mM Tris/HCl (pH 7.5), 7 mM $MgCl_2$, 20 mM KCl, 7 mM 2-mercaptoethanol], 125 μg/ml pUC19 and 1.6 units/μl SmaI (Toyobo) was incubated at 30° C. for 2 hours. Then, the DNA was purified by phenol treatment and ethanol precipitation and dissolved in 80 μl of distilled water. Thereto was added 10 μl of 10-fold concentrated dephosphorylation buffer and 10 μl of 0.4 units/μl alkaline phosphatase to make a total volume of 100 μl, and the reaction was allowed to proceed at 65° C for 30 minutes. Then, the DNA was purified by phenol treatment and ethanol precipitation and dissolved in 20 μl of TE buffer (hereinafter, pUC19/SmaI).

Then, the DNA were subjected to ligation reaction. Thus, a reaction mixture (10 μl) comprising ligation buffer [30 mM Tris/HCl (pH 7.8), 10 mM DTT, 1 mM ATP], 10 μg/ml pUC19/SmaI, 60 μg/ml repaired ntp-DNA/DNase I and 600 units/ml T4 DNA ligase (Promega) was incubated at 16° C. for 24 hours. Then, the enzyme was inactivated by 10 minutes of treatment at 65° C. A portion of this ligation reaction mixture was used to transfect *Escherichia coli* IM109 and transformant selection was performed on LB ampicillin plates [1% tryptone, 0.5% yeast extract, 1% NaCl, 50 μg/ml ampicillin, 40 μg/ml isopropyl-β-D-thiogalactopyranoside (IPTG), 40 μg/ml 5-bromo-4-chloro-3-indolyl-β-D-galactoside (X-gal), 1.5% agar].

In the above selection, positive colonies were isolated and plasmids were prepared [cf. Sambrook et al., Molecular Cloning (A Laboratory Manual)]. As a result, plasmid DNA could be isolated with three ntp-DNA-derived DNA fragments cloned therein. They were designated as pTL34, pTL57 and pTL85, respectively.

EXAMPLE 15
(Base sequence determination of ntp-DNA)

The base sequences of the ntp-DNA-derived DNA inserted in pTL34, pTL57 and pTL85, respectively, were determined by the dideoxy terminator method. The sequences determined are shown in the Sequence Listing under SEQ ID NO:1, NO:2 and NO:3, respectively Based on these results, it could be established that the product ntp-DNA cloned in pTL34 comprises a repetitive sequence of 8 bases, that the product cloned in pTL57 comprises a repetitive sequence of 12 bases, and that the DNA cloned in pTL85 comprises a sequence similar to a repetitive sequence.

Then, the base sequences shown in the Sequence Listing under SEQ ID NO:1, NO:2 and NO:3 were examined for homology using the Genbank database. These sequences were found preserved in a wide range from lower animals to higher animals, as shown in Table 4, Table 5 and Table 6, respectively. It was further found that microsatellite DNA occurring in the vicinity of the centromere were found existing in these sequences, and it was thus suggested that they might possibly have a genetically important possibility.

EXAMPLE 16
(Screening of repetitive sequences using ntp-DNA as a probe)

Exchange buffer [50 mM imidazole/HCl (pH 6.4), 18 mM $MgCl_2$, 5 mM dithiothreitol, 0.1 mM spermidine HCl, 0.1 mM EDTA] was added to 20 μg/ml ntp-DNA, together with 0.1 mM ADP, 1 nM ATP, 1 μM [γ-$^{32}$P]ATP (111 TBq/mmol), 4.8% polyethylene glycol 8000 and 400 units/ml T4 polynucleotide kinase. The mixture was incubated at 37° C for 30 minutes and then the reaction was terminated by addition of EDTA to a final concentration of 20 mM. The DNA was recovered by phenol treatment and ethanol precipitation and used as a hybridization probe.

Then, for repetitive sequence screening, plaque hybridization was performed. First, 50 ml of NZYM medium [1% casein (produced by enzymatic hydrolysis), 0.5% NaCl, 0.5% yeast extract, 0.1% casamino acids, 0.2% $MgSO_4·7H_2O$, pH 7.0] supplemented with 20t maltose was inoculated with *Escherichia coli* Y1090 (r-), followed by 5 hours of cultivation at 37° C. Cells were harvested by 10 minutes of centrifugation at 4,000×g and suspended in 0.01 M $MgSO_4$. This cell suspension was blended with a tomato cDNA library λ phage solution (Clontech; CLFL1083b) appropriately diluted with SM [0.58% NaCl, 0.2% $MgSO_4·7H_2O$, 50 mM Tris/HCl (pH 7.5), 0.01% gelatin] and the mixture was incubated at 37° C. for 20 minutes. This was added to NZCYM low-agar medium and the whole was layered on NZYM agar medium, followed by overnight cultivation at 37° C. A nitrocellulose filter (Millipore) was placed on the culture plate for 1. minute, then peeled off gently and dried at room temperature for 20 minutes. Thereafter, it was placed on a filter paper (Whatman 3 MM, product of Whatman) impregnated with a denaturing solution [0.2 N NaOH, 1.5 M NaCl] and, after 5 minutes of standing in that state, it was then placed on a 3 MM filter paper impregnated with a neutralizing solution [3 M NaCl, 0.3 M trisodium citrate dihydrate (20×SSC), 2 M Tris/HCl (pH 7.5)] and allowed to stand for 5 minutes. The filter was immersed in the neutralizing solution for 1 minute and then in 2×SSC for 5 minutes, and dried on a 3 MM filter paper. The filter was sandwiched between two sheets of 3 MM filter paper and dried in a vacuum oven under suction at 80° C. for 2 hours. The dried filter was then sufficiently moistened with hybridization buffer [50 mM HEPES/NaOH (pH 7.0), 0.2% polyvinylpyrrolidone, 0.2% Ficoll 400, 0.2% calf serum albumin, 100 μg/ml denatured salmon sperm DNA, 50% formamide], 50 ml of the hybridization buffer was added and, after sealing, the whole was allowed to stand overnight at 42° C. Thereafter, the hybridization buffer was drained off, 10 ml of the hybridization buffer supplemented with the hybridization probe heated at 100° C. for 5 minutes and then ice-cooled was added, and the whole was again sealed and incubated overnight at 42° C. Then, the filter was immersed in washing solution 1 (2×SSC, 0.1% SDS) for 1 hour and then in washing solution 2 (0.5×SSC, 0.1% SDS) at 50° C. for 2 hours for washing. This filter was dried on a sheet of 3 MM filter paper and assayed for positive plaques by autoradiography. As a result, a positive plaque was identified and it was thus established that the ntp-DNA can serve as a probe in microsattelite DNA screening, for instance.

This positive plaque was transferred to 1 ml of SM using a Pasteur pipet, one drop of chloroform was added, and the mixture was allowed to stand at room temperature for 1 hour. This was appropriately diluted with SM, the dilution and 100 μl of the cell suspension were added to 500 ml of NZCYM medium, and the whole mixture was incubated overnight at 37° C. Thereto was added 10 μl of chloroform, cells were harvested by centrifugation (7,870×g, 10 minutes) and the supernatant was recovered. To this supernatant was added 30 μl of buffer L1 (20 mg/ml RNase A, 6 mg/ml DNase I, 0.2 mg/ml calf serum albumin, 10 mM EDTA, 100 mM Tris/HCl, 300 mM NaCl, pH 7.5), followed by 30 minutes of incubation at 37° C. Then, 2 ml of ice-cooled buffer L2 (30% polyethylene glycol 6000, 3 M NaCl) and the mixture was allowed to stand on ice for 1 hour, followed by centrifugation (17,700×g, 15 minutes, 4° C.). The sediment thus recovered was suspended in 1 ml of buffer L3 (100 mM Tris/HCl, 100 mM NaCl, 25 mM EDTA, pH 7.5), 1 ml of solution L4 (4% SDS) was added, and the mixture was incubated at 70° C. for 10 minutes. After cooling on ice, 1 ml of solution L5 (2.25 M potassium acetate buffer, pH 4.8) was added and, after mixing, the mixture was centrifuged (21,600×g, 30 minutes, 4° C.) and the supernatant was recovered. Said supernatant was applied to a QIAGEN TIP-20 column (Qiagen) equilibrated beforehand with buffer QBT (750 mM NaCl, 50 mM MOPS, 15% ethanol, pH 7.0, 0.15% Triton X-100), for column chromatography. Then, the column was washed with 2 ml of buffer QC (1 M NaCl, 50 mM MOPS, 15% ethanol, pH 7.0) and DNA was eluted with 1.5 ml of buffer QF (1.25 M NaCl, 50 mM Tris/HCl, 15% ethanol, pH 8.5). To the eluate was added 0.8 volume of isopropanol, the mixture was allowed to stand at −20° C. for 20 minutes and then centrifuged (21,600×g, 30 minutes, 4° C.) for DNA recovery. The DNA sediment was washed with 70% ethanol, dried and dissolved in 10 μl of TE buffer [10 mM Tris/HCl (pH 8.0), 1 mM EDTA]. The present inventors designated this λ phage as λTL2 DNA.

Then, this λTL2 DNA was subjected to base sequence determination. The dideoxy terminator method referred to above was used. The commercial λgt11 primer was used as a primer. As a result, an ntp-DNA-derived repetitive sequence was found. It was thus verified that the ntp-DNA can serve as a probe for the screening of the repetitive sequence.

EXAMPLE 17
(High frequency recombination with ntp-DNA)

A reaction mixture prepared by adding buffer BM [50 mM Tris/HCl (pH 7.5), 10 mM MgCl$_2$, 100 mM NaCl, 1 mM dithiothreitol] and 2,000 units/ml BamHI (Toyobo) to 25 μg of the plasmid pCH110 to make a total volume of 100 μl was incubated at 37° C. for 2 hours to allow the reaction to proceed. Then, the DNA was recovered by phenol treatment and ethanol precipitation. This was dissolved in 25 μl of TE buffer [10 mM Tris/HCl (pH 8.0), 1 mM EDTA]. A reaction mixture (2.5 ml) comprising the DNA solution (25 μl), PCR buffer [10 mM Tris/HCl (pH 8.3), 50 mM KCl, 3.5 mM MgCl$_2$, 0.001% gelatin], deoxyribonucleotides [dATP, dCTP, dGTP and dTTP (all in final concentration 200 μM)], 1 nM G1 primer, 1 nM G2 primer and 25 units/ml AmpliTaq DNA polymerase was prepared. This was overlayed with an equal volume of mineral oil (Sigma), and thermal cycling was performed under the following conditions: 30 cycles, each consisting of 1 minute at 95° C., 2 minutes at 50° C. and 3 minutes at 72° C. Then, the mineral oil was removed using an equal volume of chloroform, and the DNA was recovered by phenol treatment and ethanol precipitation and dissolved in 20 μl of TE buffer. This roughly purified DNA solution was purified by the cesium chloride-ethidium bromide equilibrium density gradient centrifugation method mentioned hereinabove. As a result, 20 μg of a DNA containing the GALL promoter sequence of baker's yeast upstream of the β-galactosidase gene, and the transcription termination signal CYC1 terminator sequence downstream from that gene was obtained. This DNA was dissolved in 20 μl of TE buffer. The whole amount of the solution was used to prepare a reaction mixture by adding thereto buffer A [10 mM KCl, 10 mM (NH$_4$)$_2$SO$_4$, 20 mM Tris/HCl (pH 8.8), 6 mM MgCl$_2$, 0.1% X-100 (all in final concentration)], deoxyribonucleotides [dATP, dCTP, dGTP and dTTP (all in final concentration 200 μM)] and 20 units/ml *Thermococcus litoralis* DNA polymerase to make a total volume of 2 ml. The reaction mixture was heated at 74° C. for 3 hours to thereby allow the reaction to proceed. Then, the DNA was recovered by phenol treatment and ethanol precipitation and dissolved in 20 μl of TE buffer. This roughly purified DNA solution was purified by the cesium chlorideethidium bromide equilibrium density gradient centrifugation method mentioned above and dissolved in 20 μl of TE buffer.

YPD medium (20 ml; 1% yeast extract, 2% peptone, 2% glucose) was inoculated with baker's yeast, followed by overnight culture at 30° C. Then, 2 ml of the culture was transferred to 200 ml of YPD medium, followed by further overnight incubation at 30° C. This culture fluid was centrifuged at 400×g for 5 minutes to thereby harvest yeast cells. To the sediment was added 20 ml of SED solution (1 M sorbitol, 25 mM EDTA, 50 mM dithiothreitol) to give a cell suspension, which was incubated at 30° C. for 10 minutes. Yeast cells were again harvested by centrifugation under the same conditions as mentioned above and suspended in 20 ml of 1M sorbitol. Again, yeast cells were collected by centrifugation and suspended in 20 ml of SCE solution [1 M sorbitol, 100 mM citric acid/NaOH (pH 5.8), 10 mM EDTA]. Thereto was added 0.2 ml of Glusulase, and the mixture was incubated at 30° C. for 1 hour. This solution was centrifuged at 300×g for 5 minutes to thereby collect yeast spheroplast cells. The sediment was washed with two 20-ml portions of 1 M sorbitol and finally washed with 20 ml of STC solution [1 M sorbitol, 10 mM CaCl$_2$, 10 mM Tris/HCl (pH 7.5)]. The sediment was suspended in 1 ml of STC solution and the suspension was divided into aliquots of 100 μl. To each aliquot was added 5 μl of the DNA solution mentioned above and the mixture was allowed to stand at room temperature for 10 minutes. Then, 1 ml of PEG solution [20% polyethylene glycol 3300, 10 mM CaCl$_2$, 10 mM Tris/HCl (pH 7.4)] was added and the resultant mixture was allowed to stand at room temperature for 10 minutes, followed by centrifugation (300×g, 5 minutes). The sediment was suspended in 150 μl of SOS medium (prepared from 10 ml of 2 M sorbitol, 0.1 ml of 1 M CaCl$_2$, 6.7 ml of YPD medium, 27 μl of 1% leucine solution and 3.17 ml of distilled water). This suspension was incubated at 30° C. for 20 minutes and added to 6 ml of SYG agar medium [18.2% sorbitol, 2% agar, 0.67% yeast nitrogen base (amino acid-free), 2% glucose, 0.001% adenine, 0.004% uracil] melted in advance at 45° C., and the mixture was layered on SYG agar plate medium and incubated at 30° C. for 3 days.

A colony taken from the culture plate medium was inoculated into 5 ml of YPD medium. After overnight culture at 30° C., the culture was centrifuged at 400×g for 5 minutes and the sediment was suspended in 250 μl of BK buffer [100 mM Tris/HCl (pH 8.0), 1 mM dithiothreitol, 20% glycerol]. To the suspension was added 12.5 μl of PMSF solution (40 mM phenylmethylsulfonyl fluoride) and the mixture was stirred vigorously. Again, 250 μl of BK buffer was added, followed by thorough stirring. The mixture was centrifuged at 17,700×g for 15 minutes and the supernatant was transferred to a separate vessel. BK buffer (50 μl) and 0.9 ml of Z buffer (1.61% $Na_2HPO_4 \cdot 7H_2O$, 0.55% $NaH_2PO_4$, 0.075% KCl, 0.0246% $MgSO_4$, 0.27% β-mercaptoethanol) were added to 50 μl of said supernatant, followed by 5 minutes of incubation at 28° C. Then, 0.2 ml of ONPG solution (4 mg/ml onitrophenyl-β-D-galactopyranoside) to thereby initiate the reaction, and incubation was continued at 28° C. Thirty minutes later, the reaction was terminated by adding 0.5 ml of 1 M $Na_2CO_3$ solution. Then, absorbance measurement was performed at 420 nm. Protein determination was also made by Bradford's dye binding assay [Bradford, Analytical Biochemistry, volume 72, pages 248–254 (1976)]. Based on the absorbance and protein assay data, the specific activity of μ-galactosidase in the cell extracts was calculated. As a result, for 4 out of 20 samples, μ-galactosidase activity was verified (Table 6). This proved that the μ-galactosidase gene had been introduced into the yeast chromosome through the intermediary of the ntp-DNA terminally added. Furthermore, these μ-galactosidase activity-exhibiting strains were subjected to double in situ hybridization using a fluorescence-labeled (rhodamine-labeled) probe complementary to the μ-galactosidase gene sequence and a fluorescence-labeled (fluoresceine-labeled) probe complementary to the ntp-DNA and, as a result, the occurrence of the ntp-DNA in the yeast chromosome in close vicinity to the μ-galactosidase gene could be confirmed.

EXAMPLE 18

(Synthesis of chromosomal DNA)

A reaction mixture (1 ml) comprising 10 mM KCl, 10 mM $(NH_4)_2SO_4$, 20 mM Tris-HCl (pH 8.8), 6 mM $MgCl_2$, 0.1% octoxynol (Triton X-100; Sigma), deoxyribonucleotide triphosphates [0.2 mM dATP, 0.2 mM dTTP, 0.2 mM dGTP, 0.2 mM dCTP] and 20 units/ml *Thermococcus litoralis* DNA polymerase (trademark: Vent DNA polymerase; New England Biolabs) was heated at 74° C. for 3 hours to thereby allow the reaction to proceed.

Then, a portion (20 μl) of the reaction mixture was taken and subjected to 1% agarose gel electrophoresis [Sambrook et al., Molecular Cloning (A Laboratory Manual), Cold Spring Harbor Laboratory Press, published 1989] and the subsequent staining with 0.5 μg/ml ethidium bromide, followed by photography using an ultraviolet lamp. As a result, it was confirmed that DNA of 100 to 50,000 base pairs in size had been synthesized.

The remaining 980-μl portion was used for DNA purification by phenol treatment, washing with chloroform, ethanol precipitation and cesium chloride equilibrium density gradient centrifugation [Haruo Koseki et al., "Bunshi Idengaku Jikkenho (Experiments in Molecular Biology)", Kyoritsu Shuppan, published 1983]. Thus was obtained about 20 μg of DNA.

(Base sequence of chromosomal DNA)

Half of the DNA fraction obtained was used for DNA base sequence determination (Bunshi Idengaku Jikkenho). The thus-revealed partial base sequences are shown in the sequence listing under SEQ ID NO:1, NO:2 and NO:3. The base sequences were variegated, involving repetitive sequences and, in some parts, nonrepetitive (unique) sequences. To be more concrete, the DNA obtained were found to have a region comprising a number of repetitions of the eight base pairs [CTAGATAT] (cf. SEQ ID No:1). The region of these repetitions is considered to function as the centromere. It was also revealed that they have a region comprising the guanine-rich repetitive sequence [TTGGGG]. It is supposed that this region should function as the telomere. In addition, they have the repetitive sequences [TAGATATCTATC](nucleotides 15 to 26 of SEQ ID NO. 3, [GGAAT], etc.

(Introduction of chromosomal DNA into cells)

The remaining half of the DNA fraction obtained was introduced into cells (human HeLa cells) by the calcium phosphate coprecipitation method (after introduction, such DNA are bound to the protein histone) and the cells were subcultured. After about 10 divisions, DNA was extracted from the cells and DNA searching was performed by the Southern blotting method (Bunshi Idengaku Jikkenho) using $(CTAGATAT)_{15}$ as a probe. As a result, such DNA were found remaining intracellularly.

This clearly indicates that among the DNA obtained, there are chromosomal DNA functioning as chromosomes. (If the DNA synthesized are lacking in the centromere, telomere or replication origin region, said DNA can no more function as chromosomal DNA and none of them can remain after cell division. Searching with $(CTAGATAT)_{15}$ as a probe must fail to detect any of the DNA.) Those DNA already existing in HeLa cells (i.e., chromosomal DNA of HeLa cells) differ in length, hence are distinguishable, from the DNA introduced in this example. No confusion will arise.

Then, in situ hybridization was performed using a fluorescence-labeled probe and a sufficiently high-powered microscope, whereby chromosomes in the mitotic phase could be observed.

EXAMPLE 19

The procedure of Example 18 was followed using *Thermus aquaticus* DNA polymerase [Ampli Taq DNA polymerase (trademark), Perkin Elemer] (in lieu of *Thermococcus litoralis* DNA polymerase. The results obtained were similar to those of Example 18.

EXAMPLE 20

The procedure of Example 18 was followed using *Thermus thermophilus* DNA polymerase [Tth DNA polymerase (trademark), Promega] in lieu of *Thermococcus litoralis* DNA polymerase. The results obtained were similar to those of Example 18.

EXAMPLE 21

In this example, a method is described according to which chromosomal DNA are synthesized intracellularly and are allowed as such to mature into chromosomes.

Figure 10:
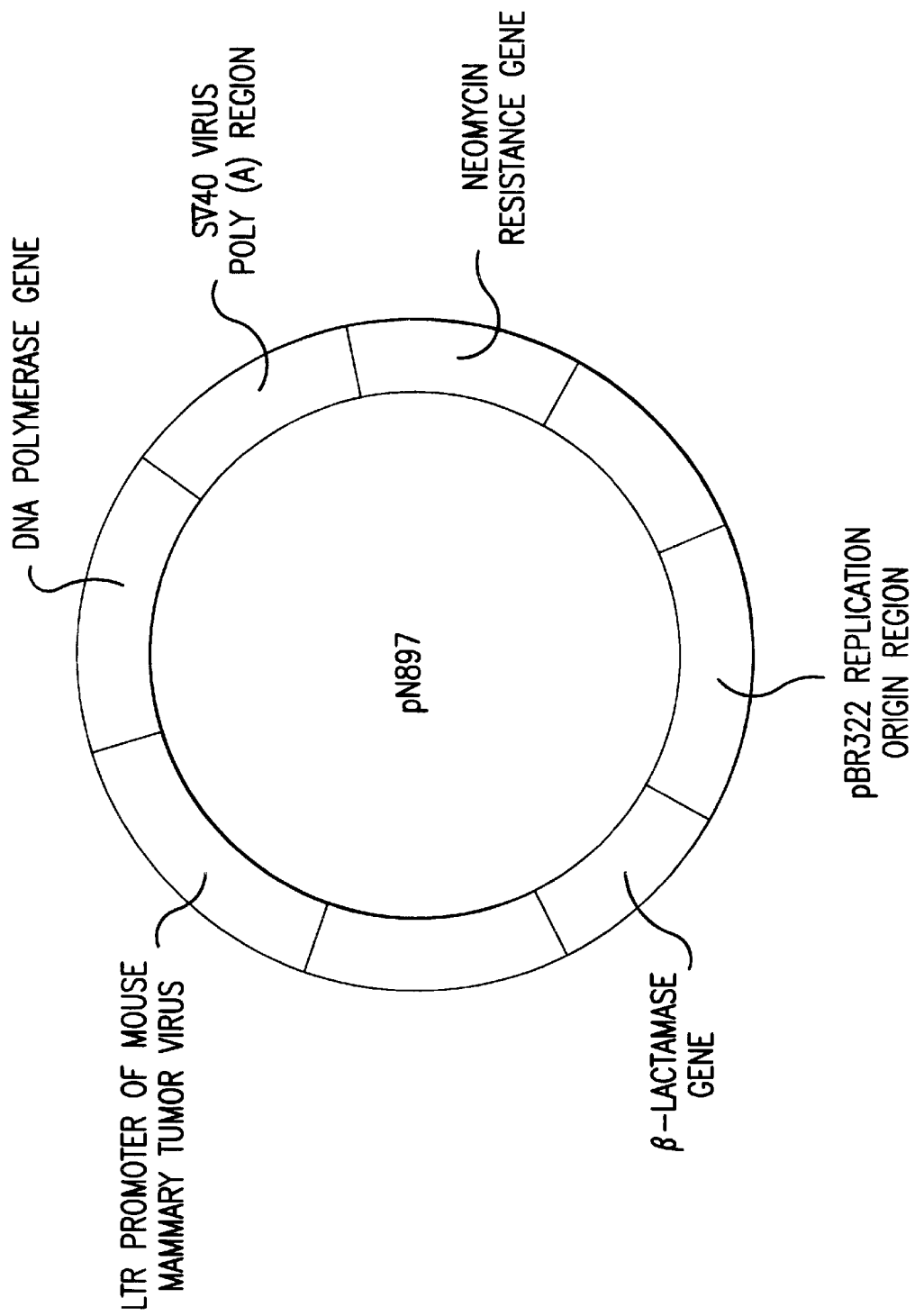
FIG. 10 is a schematic representation of the expression vector pN897.

A plasmid, pN897, was constructed by inserting the *Thermococcus litoralis* DNA polymerase gene into an expression vector for use in eukaryotic cells (cf. FIG. 10). (This construction is obvious to the one skilled in the art. See, for example, Japanese Kokai Tokkyo Koho H06-7160 etc. The following may also be used: GenBank accession number: M74196; ATCC accession No.: 68487; ATCC accession No.: 68447.) Said plasmid was introduced into simian COS7 cells by the conventional calcium phosphate method. The introduction into COS7 cells was confirmed by their growth in a medium (Dulbecco medium containing 20% fetal bovine serum) containing 400 μg/ml G418, with the neomycin resistance gene of PN897 as the selective marker.

COS7 cells with pN897 introduced therein were cultured in a medium containing 10 μg/ml dexamethasone for 2 days to activate an LTR promoter of the mouse mammary tumor virus in pN897. This lead to confirmation, by Western blotting, of the production of the *Thermococcus litoralis* DNA polymerase protein within COS7 cells. It was confirmed, by the same method as used in Example 18, that the protein synthesized chromosomal DNA within cells and some of them functioned as chromosomes of the cells.

What is claimed is:

1. A method of synthesizing polydeoxyribonucleotides which comprises heating a reaction mixture containing at least deoxyribonucleotide dCTP or dGTP of the deoxyribonucleotides selected from the group consisting of dCTP, dGTP, dATP and dTTP and containing a thermostable polymerase stable at temperatures about 60 degrees celsius or at temperatures exceeding 60 degrees celsius, but containing no template and/or no primers, for a predetermined period of time to thereby cause polymerization of said deoxyribonucleotides, the polydeoxyribonucleotides thus synthesized containing at least dG of dC as a comonomer unit component.

2. A method of synthesizing polydeoxyribonucleotides as claimed in claim 1, wherein said thermostable deoxyribonucleotide polymerase comprises deoxyribonucleotide polymerase derived from a bacterial strain belonging to the genus Thermococcus and/or deoxyribonucleotide polymerase derived from a bacterial strain belonging to the genus Thermus.

3. A method of synthesizing polydeoxyribonucleotides as claimed in claim 2, wherein said bacterial strain belonging to the genus Thermococcus is of the species *Thermococcus litoralis*.

4. A method of synthesizing polydeoxyribonucleotides as claimed in claim 2, wherein said bacterial strain belonging to the genus Thermus comprises a *Thermus thermophilus* strain and/or a *Thermus aquaticus* strain.

5. A method of synthesizing polydeoxyribonucleotides as claimed in claim 1, wherein the polymerization reaction is allowed to proceed at a temperature of about 20° C. to 90° C.

6. A method of synthesizing polydeoxyribonucleotides as claimed in claim 1, wherein the polymerization reaction is allowed to proceed at a temperature of about 60° C. to 90° C.

7. A method of synthesizing polydeoxyribonucleotides as claimed in claim 1, wherein the polymerization reaction is allowed to proceed under weakly acidic, neutral or weakly alkaline conditions.

8. A method of synthesizing polydeoxyribonucleotides as claimed in claim 1, wherein the polymerization reaction is allowed to proceed at pH 6 to 10.

9. A method of synthesizing polydeoxyribonucleotides which comprises the steps of:
(a) inserting a gene coding for a thermostable polymerase stable at temperatures about 60 degrees celsius or at temperatures exceeding 60 degrees celsius into an expression vector,
(b) introducing the resulting recombinant expression vector into cells,
(c) causing expression of said gene in said cells to thereby produce said polymerase, and
(d) heating a reaction mixture containing at least deoxyribonucleotide dCTP or dGTP of the deoxyribonucleotides selected from the group consisting of dCTP, dGTP, dATP and dTTP, but containing no template and/or no primers, for a predetermined period of time in the presence of the thus-produced polymerase outside said cells to thereby cause polymerization of the deoxyribonucleotides, the polydeoxyribonucleotide thus synthesized containing at least dC or dG as a comonomer unit component.

10. A method of synthesizing polydeoxyribonucleotides as claimed in claim 9, wherein said thermostable deoxyribonucleotide polymerase comprises deoxyribonucleotide polymerase derived from a bacterial strain belonging to the genus Thermococcus and/or deoxyribonucleotide polymerase derived from a bacterial strain belonging to the genus Thermus.

11. A method of synthesizing polydeoxyribonucleotides as claimed in claim 10, wherein said bacterial strain belonging to the genus Thermococcus is of the species *Thermococcus litoralis*.

12. A method of synthesizing polydeoxyribonucleotides as claimed in claim 10, wherein said bacterial strain belonging to the genus Thermus comprises a *Thermus thermophilus* strain and/or a *Thermus aquaticus* strain.

13. A method of synthesizing chromosomal DNA which comprises heating a reaction mixture containing at least deoxyribonucleotide dCTP or dGTP of the deoxyribonucleotides selected from the group consisting of dCTP, dGTP, dATP and dTTP and a thermostable polymerase stable at temperatures about 60 degrees celsius or at temperatures exceeding 60 degrees celsius, but containing no template and/or no primers, for a predetermined period of time to thereby cause polymerization of said deoxyribonucleotides, the polydeoxyribonucleotide thus synthesized containing, in one and the same molecule thereof, at least dC or dG as a comonomer unit component, a centromere region and a telomere region, both independently comprising a repetitious DNA sequence, and a replication origin region.

14. A method of synthesizing chromosomal DNA which comprises the steps of:
(a) inserting a gene coding for a thermostable polymerase stable at temperatures about 60 degrees celsius or at temperatures exceeding 60 degrees celsius into an expression vector,
(b) introducing the resulting recombinant expression vector into cells,
(c) causing expression of said gene in said cells to thereby produce said polymerase, and
(d) heating a reaction mixture containing at least deoxyribonucleotide dCTP or dGTP of the deoxyribonucleotides selected from the group consisting of dCTP, dGTP, dATP and dTTP, but containing no template and/or no primers, for a predetermined period of time in the presence of the thus-produced polymerase outside said cells to thereby cause polymerization of the deoxyribonucleotides, the polydeoxyribonucleotide thus synthesized containing, in one and the same molecule thereof, at least dC or dG as a comonomer unit component, a centromere region and a telomere region, both independently comprising a repetitious DNA sequence, and a replication origin region.

15. A method of synthesizing chromosomal DNA as claimed in Claims 13 or 14, wherein said thermostable deoxyribonucleotide polymerase comprises deoxyribonucleotide polymerase derived from a bacterial strain belonging to the genus Thermococcus and/or deoxyribonucleotide polymerase derived from a bacterial strain belonging to the genus Thermus.

16. A method of synthesizing chromosomal DNA as claimed in claim 15, wherein said bacterial strain belonging to the genus Thermococcus is of the species *Thermococcus litoralis*.

17. A method of synthesizing chromosomal DNA as claimed in claim 15, wherein said bacterial strain belonging to the genus Thermus comprises a *Thermus thermophilus* strain and/or a *Thermus aquaticus strain*.

18. A method of producing chromosomes which comprises introducing into cells the chromosomal DNA obtained by the method claimed in one of claims 13 or 14 when said chromosomal DNA is one synthesized extracellularly, or allowing said chromosomal DNA to mature into a chromosome intracellularly when said chromosomal DNA is one synthesized intracellularly, to thereby cause a protein, which is another essential component of chromosomes, to bind to said chromosomal DNA, said chromosomal DNA containing, in one and the same molecule thereof, at least dC or dG as a comonomer unit component, a centromere region and a telomere region, both independently comprising a repetitious DNA sequence, and a replication origin region.

19. The method of claim 18, wherein the protein is a histone.

20. A method of producing chromosomes which comprises introducing into cells the chromosomal DNA obtained by the method of claim 15 when said chromosomal DNA is one synthesized extracellularly, or allowing said chromosomal DNA to mature into a chromosome intracellularly when said chromosomal DNA is one synthesized intracellularly to thereby cause a protein, which is another essential component of chromosomes, to bind to said chromosomal DNA, said chromosomal DNA containing, in one and the same molecule thereof, at least dC or dG as a comonomer unit component, a centromere region and telomere region, both independently comprising a repetitious DNA sequence, and a replication origin region.

* * * * *